United States Patent
Schroff et al.

(10) Patent No.: US 9,499,815 B1
(45) Date of Patent: Nov. 22, 2016

(54) MULTIMER FOR IMMUNOSTIMULATION

(75) Inventors: Matthias Schroff, Berlin (DE);
Burghardt Wittig, Berlin (DE);
Manuel Schmidt, Berlin (DE); Janine Loehr, Berlin (DE)

(73) Assignee: Mologen AG, Berlin (DE)

( * ) Notice: Subject to any disclaimer, the term of this patent is extended or adjusted under 35 U.S.C. 154(b) by 1317 days.

(21) Appl. No.: 12/300,295

(22) PCT Filed: May 11, 2007

(86) PCT No.: PCT/DE2007/000887
§ 371 (c)(1),
(2), (4) Date: Jun. 30, 2009

(87) PCT Pub. No.: WO2007/131495
PCT Pub. Date: Nov. 22, 2007

(30) Foreign Application Priority Data

May 11, 2006 (DE) .................. 10 2006 023 332

(51) Int. Cl.
*C12N 15/113* (2010.01)
*C12N 15/117* (2010.01)

(52) U.S. Cl.
CPC .......... *C12N 15/113* (2013.01); *C12N 15/117* (2013.01)

(58) Field of Classification Search
CPC .................................................... C07H 21/02
USPC ........................................................ 536/23.1
See application file for complete search history.

(56) References Cited

FOREIGN PATENT DOCUMENTS

| WO | WO 01/07055 | 2/2001 |
| WO | WO 02/060476 | 8/2002 |

OTHER PUBLICATIONS

Levin: "A review of the issues in the pharmacokinetics and toxicology of phosphorothiate antisense oligonucleotides", in: Biochimica et Biophysica, Acta 1489, 1999, pp. 69-84.
Heikenwalder et al.: "Lymphoid follicle destruction and immunosuppression after repeated CpG oligodeoxynucleotide administration", in: Nature Medicine, vol. 10, No. 2, Feb. 2004, pp. 187-192.
Brown et al.: Effect of Phosphorothioate Modification of Oligodeoxynucleotides on Specific Protein Binding, in: The Journal of Biological Chemistry, vol. 269, No. 43, Oct. 1994, pp. 26801-26805.
Arthur M. Krieg: "CpG motifs: the active ingredient in bacterial extracts?", in: Nature Medicine, vol. 9, No. 7, Jul. 2003, pp. 831-835.
Schmidt et al.: "Cytokine and Ig-production by CG-containing sequences with phosphorodiester backbone and dumbbell-shape", in: Allergy, 2006, pp. 56-63.

*Primary Examiner* — Jim Ketter
(74) *Attorney, Agent, or Firm* — 24IP Law Group; Timothy R DeWitt

(57) ABSTRACT

The invention relates to a multimeric non-coding nucleic acid molecule for modulating the activity of the human or animal immune system, and to a preparation process therefore and a vaccine which comprises the multimeric non-coding nucleic acid molecule.

9 Claims, 30 Drawing Sheets

SEQ ID NO: 28

SEQ ID NO: 29

Endotoxin (EU/mg DNA): 3 <1 6 8 1 1 <1

MULTIMER FOR IMMUNOSTIMULATION

The sequence listing electronically filed herewith is hereby incorporated by reference in its entirety (File Name: 12031-80520_Seq_ListCorrected2.txt; File Size: 8 KB; Date Created Jun. 18, 2013).

BACKGROUND OF THE INVENTION

Field of the Invention

The invention relates to a multimeric non-coding nucleic acid molecule for modulating the activity of the human or animal immune system, a method of preparing same, and a vaccine which contains the multimeric non-coding nucleic acid molecule.

Brief Description of the Related Art

While adaptive immune response following selection of lymphocytes specific for the respective pathogen and clonal expansion and differentiation thereof into effector cells takes effect only in a delayed fashion (3-5 days), but then offers long-lasting protection from the respective pathogen through formation of an "immunologic memory", cells of the innate immune system recognize pathogens on the basis of preserved pathogen-associated molecular patterns (PAMPs) with germ cell-encoded receptors and respond immediately. The reactions that are different for different types of cells include secretion of cytokines (e.g. IL-1, IL-6, TNF-α) and chemokines (e.g. IL-8/CXCL8, MIP-1α/β, MCP-1), activation of effector mechanisms (phagocytosis, respiratory discharge, liberation of bactericidal substances or lytic granula), expression of co-stimulatory molecules (CD80, CD86) as well as enhanced expression of MHC molecules. On the one hand, this recruits and activates effector cells capable of eliminating the invaded pathogen and, on the other hand, the cells of the adaptive immune system receive signals necessary for activation thereof.

To produce an improved immune response, CpG oligonucleotides (CpG ODN) have been used as a new class of immunomodulatory molecules. Such non-methylated CG motifs occur in bacterial DNA and represent a "danger signal" to the immune system. Being "pathogen-associated molecular patterns" (PAMPs), they mainly cause non-specific activation of the innate immune system (Krieg, Nat. Med 2003, 9: 831-835).

CpG ODNs induce a $T_H1$-accentuated immune response via the cytokines interleukin-12, interferon-γ and tumor necrosis factor α.

Immunostimulatory nucleic acid sequences (ISS) bearing the above-mentioned CpG ODNs are only a few bases in length and do not function via expression of proteins encoded thereon.

The ISS are covalently closed nucleic acid molecules. They consist of oligonucleotides, whose bases can undergo partial pairing with themselves, and one or two loops which comprise 30 bases and several CG motifs and will be referred to as carrier molecules hereinbelow.

The strong stimulation of cellular immune response allows exertion of influence on regulatory cycles which, without intervention, would result in an immune activity unsatisfactory to the patient.

Modification of CpG ODNs with phosphorothioate backbone, as used in stabilization of "CpG DNA", has a number of serious drawbacks, including in particular the toxicity being observed [Heikenwalder 2004, Levin 1999], as well as non-specific binding to proteins [Brown 1994].

For this reason, a new class of covalently closed immunostimulatory DNA has been developed (EP 1196178). These DNA molecules consist of two chemically synthesized DNA molecules having a self-complementary region at the 5' and 3' ends with palindromic overlaps so that ligation of the two DNA molecules produces a covalently closed molecule. These DNA molecules with CG motifs in the non-complementary region show similar activity as CpG ODN (enhanced expression of the surface molecules CD80, CD40, MHC on B cells and secretion of IL-6, IFN-γ, IFN-α, IL-12, TNF-α by PBMC), but, compared to CpG ODN with phosphorothioate backbone, have a somewhat different expression pattern and significantly lower toxicity in mice. However, this immunostimulatory DNA of the prior art has a number of drawbacks regarding the modulation of human or animal immune system activity. It is not always possible to modulate, especially trigger, the activity of the human or animal immune system at a desired level.

SUMMARY OF THE INVENTION

Given the above state of the art, the object of the present invention is to provide suitable immunostimulatory DNA molecules capable of triggering an improved immune response, a method for the production thereof, as well as vaccines containing said immunostimulatory DNA molecules.

In the context of the present invention immunostimulation means that the mediator and effector cells of the immune system, i.e., especially the presently known thymocytes with helper function and cytotoxic thymocytes, B cells and so-called NK (natural killer) cells, macrophages and monocytes as well as dendritic cells and precursors thereof, as well as cell populations assuming functions within the immune system, which functions have not been clarified as yet, are stimulated to show proliferation, migration, differentiation or activity through the use of nucleic acid molecules. Immunomodulation means that, in addition to general stimulation in the meaning defined above, there is also an influence on the type or character of an immune reaction, be it by involvement of an immune reaction in the process of its origin or maturing, or be it by changing a previously established reaction in its nature.

The present invention solves the object by providing a multimeric non-coding nucleic acid molecule. The multimeric molecule can be produced by means of a method comprising the following steps:

providing a 5'-phosphorylated oligodeoxyribonucleic acid sequence in water, lyophilizing until a dry residue is obtained, followed by resuspending in a buffer solution, adding a T4 DNA ligase, thereby forming a reaction mixture, and incubating the reaction mixture at 37° C. for at least 30 minutes.

Most surprisingly, the order of the above-mentioned steps results in a multimeric molecule which is better suited for use in modulating the activity of the human or animal immune system than the molecules of the prior art. A multimeric molecule in the meaning of the invention is essentially a deoxyribonucleic acid molecule, said nucleic acid molecule preferably having a length of at least 100 nucleotides, more preferably 200, especially preferably more than 300. While EP 1 196 178 discloses molecules which, in view of their stem-loop structure, can be referred to as monomers, the method according to the invention provides molecules wherein a number of such stem-loop monomer structures assemble into multimeric or oligomeric structures. Surprisingly, the resulting assemblates are effective in modulating the immune system. It was surprising that the per se simple and laboratory-typical process steps mentioned above result in the formation of effective structures. Compared to the structures according to EP 1 196 178, the multimeric molecules according to the invention represent higher molecular complexes.

In a preferred embodiment of the invention the oligomeric or multimeric assemblate, i.e., the molecule according to the invention, is characterized in that the oligodeoxyribonucleic acid sequence comprises the following sequences:
a) GTTCCTGGAG ACGTTCTTAG GAACGTTCTC CTTGACGTTG GAGAGAAC (SEQ ID NO: 1) or
b) ACCTTCCTTG TACTAACGTT GCCTCAAGGA AGGTTGATCT TCATAACGTT GCCTAGATCA (SEQ ID NO: 2), or
c) comprises an oligodeoxyribonucleic acid sequence having the base sequence AACG TTCTTCGGGG CGTT (SEQ ID NO: 3),
d) said oligodeoxyribonucleic acid sequence having a length of 40 to 1,600 nucleotides.

The multimeric assemblates in the meaning of the invention, which include the preferred sequences, are particularly suitable for stimulating the activity of the immune system in domestic animals and humans.

In a preferred fashion the base sequence according to feature c) is included in the sequence CCTAGGGGTT ACCACCTTCA TTGGAAAACG TTCTTCGGGG CGTTCTTAGG TGGTAACC CCTAGGGGTT ACCACCTTCA TTGGAAAACG TTCTTCGGGG CGTTCTTAGG TGGTAACC (SEQ ID NO: 4). Surprisingly, the presence of the above sequence results in a particularly high effect of the molecule, which effect in the meaning of the invention is understood to be activation of the immune system.

Another preferred embodiment of the invention envisages that the molecule comprises a partially single-stranded, covalently closed chain of deoxyribonucleoside residues. It is the partially single-stranded, covalently closed chain of deoxyribonucleoside residues within the assembled oligomeric or polymeric structure of the molecule that is responsible for prolonged effective activity of the molecule in a target organism wherein it has been incorporated.

Another preferred embodiment of the invention envisages that the molecule comprises the base sequence $N^1N^2CGN^3N^4$ wherein $N^1N^2$ is an element from the group of GT, GG, GA, AT or AA, $N^3N^4$ is an element from the group of CT or TT, and C is deoxycytosine, G is deoxyguanosine, A is deoxyadenosine, and T is deoxythymidine.

A particularly preferred embodiment envisages that the base sequence $N^1N^2CGN^3N^4$ is situated in the single-stranded region of the closed chain of deoxyribonucleoside residues. It is particularly these preferred molecules that show highly effective activity in stimulating the immune system.

The invention also relates to the inventive molecule covalently bound to a number of substituents, said substituents preferably being peptides, proteins, saccharides, antigenic structures, DNA and/or RNA molecules.

The invention also relates to a combination agent comprising at least one molecule according to the invention and a chemotherapeutic agent. Surprisingly, the amazingly high stimulation of the immune system by the molecule of the invention can even be improved when the agent of the invention is combined with a well-known chemotherapeutic agent and the combination agent is used against tumors. The combination agent in the meaning of the invention can also be provided in the form of a kit wherein the agent of the invention and the prior art chemotherapeutic agent are present separately. Thus, in preferred embodiments the at least two components of the kit can be applied at the same time or in a time-shifted manner. For example, administration of the combination agent according to the invention can activate the immune system in such a way that a subsequently applied chemotherapeutic agent can develop its activity especially effectively. Obviously, it is also possible to apply the chemotherapeutic agent first and subsequently administer the molecule of the invention to the human or animal organism in a time-shifted manner. For particular tumors, simultaneous administration of the molecule according to the invention and chemotherapeutic agent is preferred.

In a preferred embodiment of the invention the chemotherapeutic agent is selected from the group comprising antibodies, alkylating agents, platinum analogs, intercalating agents, antibiotics, mitosis inhibitors, taxanes, topoisomerase inhibitors, antimetabolites and/or L-asparaginase, hydroxycarbamide, mitotane and/or amanitins.

In a preferred embodiment of the invention the alkylating agents are selected from the group comprising
nitrogen mustard derivatives, especially
cyclophosphamide,
ifosfamide,
trofosfamide,
melphalan and/or
chlorambucil
akylsulfonates, especially
busulfan and/or
treosulfan
nitrosoureas, especially
carmustine,
lomustine,
nimustine,
estramustine and/or
streptozotocin
procarbazine and dacarbazine,
temozolomide and/or
thiotepa.

The alkylating agents have an especially high effect on tumors, thereby inhibiting growth thereof.

In a preferred embodiment of the invention the platinum analogs are selected from the group comprising:
cisplatin,
carboplatin and/or
oxaliplatin.

Another preferred embodiment of the invention envisages that the intercalating agents are selected from the group comprising:
anthracyclines, especially
doxorubicin (adriamycin),
daunorubicin,
epirubicin and/or
idarubicin,
mitoxantrone,
amsacrin and/or
doxifluridine.

Another preferred embodiment of the invention envisages that the antibiotics are selected from the group comprising:
bleomycin,
actinomycin D (dactinomycin) and/or
mitomycin.

In another preferred embodiment of the invention, it can be advantageous to select the mitosis inhibitors from the group comprising:
alkaloids of *Vinca rosea*, especially
vinorelbine,
vincristine (oncovin), vinblastine and/or
vindesine.

In another particularly preferred embodiment of the invention the taxanes are selected from the group comprising:
paclitaxel and/or
docetaxel.

Furthermore, it can be preferred to select the topoisomerase inhibitors from the group comprising:
topoisomerase I inhibitors, especially
camptothecin,
topotecane and/or
irinotecane and/or
topoisomerase II inhibitors, especially
etoposide
teniposide.

It is also preferred that the antimetabolites in a special embodiment of the invention are selected from the group comprising:
folic acid antagonists, especially
methotrexate,
pyrimidine analogs, especially
5-fluorouracil,
capecitabine,
cytosine arabinoside (cytarabine) and/or
gemcitabine,
purine analogs, especially
6-thioguanine,
pentostatine,
azathioprine,
6-mercaptopurine,
fludarabine and/or
cladribine.

The invention also relates to a kit comprising the molecule of the invention and the chemotherapeutic agent, optionally together with information relating to combining the contents of the kit. As set forth above, the invention also relates to a pharmaceutical agent comprising the molecule of the invention or the combination agent, optionally together with a pharmaceutically tolerable carrier.

Furthermore, the invention relates to the use of said molecule, combination agent or pharmaceutical agent for the production of an agent for modulating a human or animal immune system or modulating the activity of such an immune system. Modulation of the human or animal immune system is understood to be any influence on the immune system that results in an inhibiting effect of the immune system on tumors or cancers. Modulating the activity of the immune system can be understood synonymously or describes activities of the immune system well-known to those skilled in the art, which are directed against tumors and, surprisingly, increased in strength by the agents according to the invention. More specifically, modulation is therefore a stimulation or an enhancement of effects of the immune system or of the immune system itself. Thus, in a preferred embodiment, the agents according to the invention can be used to stimulate the T cell-mediated immune response but also the T cell-independent immune response. In a preferred embodiment of the invention this process may comprise proliferation of B cells or B cell activation.

In a particularly preferred embodiment, modulating the activity of the immune system gives rise to stimulation in such a way that cytokines are secreted, or secreted at higher levels. It can be particularly preferred to use the molecule of the invention or the combination agent according to the invention as an adjuvant in therapeutic or prophylactic vaccination. In a particularly effective way, the agents of the invention can be used in the treatment of cell growth disorders, and in a preferred embodiment the cell growth disorder is a tumor disease. In a preferred fashion the tumor disease is a disease selected from the group comprising tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarial carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, Hodgkin's disease, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppressionrelated malignancy comprising AIDS-related malignancy such as Kaposi sarcoma, AIDS-associated lymphomas, AIDS-associated lymphomas of the central nervous system, AIDS-associated Hodgkin's disease and AIDS-associated anogenital tumors, transplantation-related malignancy, metastasized tumors comprising brain metastases, lung metastases, liver metastases, bone metastases, pleural and pericardial metastases, and malignant ascites.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
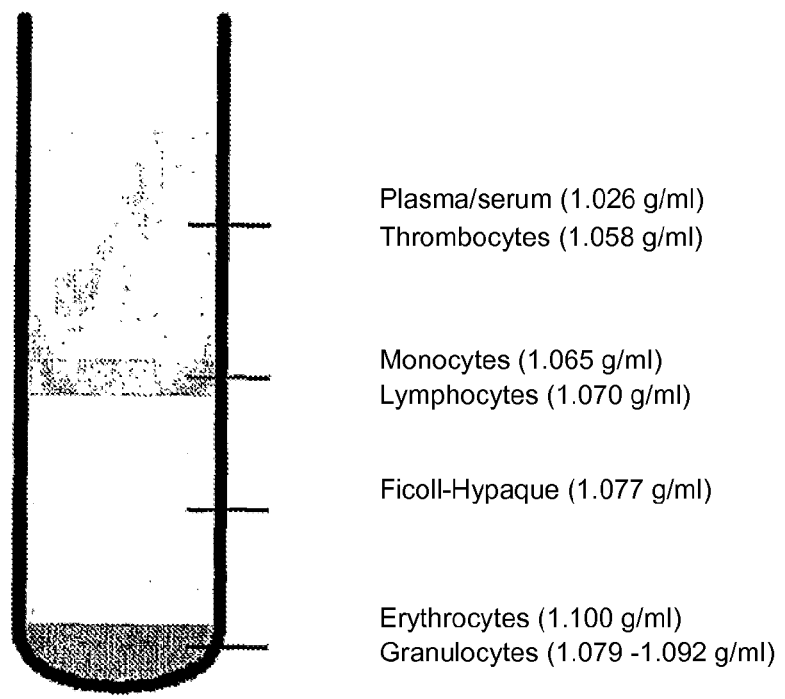
FIG. 1 shows fractions obtained using isopyknic centrifugation of the separation medium with a layer of dilute leukocyte concentrate on top, it is possible to separate the different components according to the different density thereof.

Without intending to be limiting, the invention will be explained in more detail below with reference to the examples.

The equipment, materials and solutions required for the individual methods are represented under the respective method. The following table includes a list of equipment and materials, which have been used and do not pertain to a specific method, and chemicals and solutions required for the preparation of the solutions:

TABLE

| Equipment, materials, chemicals and solutions used | |
|---|---|
| Name | Manufacturer/Supplier |
| Equipment | |
| Biofuge Pico | Hereaus |
| Digital pH meter | Knick |
| Hotstage HLC Progress | Sigma |
| Magnetic stirrer IKA MAG REO | Janke and Kunkel |
| Top-loading balance | Sartorius |
| Pipettboy Accu Jet | Brand |
| Vortex Genie 2 | Scientific Instruments |
| Materials | |
| Disposable pipettes 5, 10, 25 ml | Coming B.V. Life Sciences |
| Bottle-top filter 0.2 μm | Nunc |
| Pipette tips of various sizes | Roth |
| Reaction vessels 0.5 ml, 1.5 ml | Eppendorf |
| Syringes (sterile, 10 ml, 100 ml) | Becton Dickinson |
| Syringe filter 0.45/0.2 μm | Schleicher & Schüll |
| Chemicals, solutions | |
| APS | Life Technologies |
| ATP | Sigma |
| Blasticidin S (10 mg/ml) | Invivogen |
| Boric acid | Roth |
| BSA | Sigma |
| Coomassie Brilliant Blue R-250 | Serva |
| DMEM medium | BioWhittaker |
| Ethanol, absolute | J. T. Baker |
| Ethidium bromide | Sigma |
| FBS | BioWhittaker |
| MgCl$_2$ | Roth |
| Na$_2$EDTA•2 H$_2$O | Roth |
| NaCl | Roth |
| NaN$_3$ | Merck |
| Sodium acetate (anhydrous) | Roth |
| PBS free of Ca and Mg | BioWhittaker |
| Penicillin/streptomycin | BioWhittaker |
| RPM medium | BioWhittaker |
| Saccharose | Roth |
| Hydrochloric acid (HCl) 25% | Roth |
| Sulfuric acid (H$_2$SO$_4$) | Roth |
| TAE buffer (50×) | AppliChem |
| TEMED | Roth |
| Tris Ultra | Roth |
| Trypsin solution | BioWhittaker |
| Tween 20 | Roth |

ODNs and dSLIMs Used, Sequence Selection Using Mfold

Many of the sequences used to produce model molecules for the investigation of the structure of dSLIM were constructed using the "mfold" software available in the WWW. It is a program used to predict the secondary structure of nucleic acids based on thermodynamic data [Zuker, 2003]. The sequences of the DNA 58 nucleotides in length, referred to as ODN hereinbelow, used to synthesize dSLIM were input as linear DNA in "DNA mfold", using standard settings and the following parameters: temperature 37° C., ion concentration 150 mM Na$^+$ and 0.5 mM Mg$^{2+}$, oligomer correction.

The sequence of dSLIM-30L1 was used as a basis for the model molecules to investigate the formation of G structures. Initially, the latter were modified in such a way that consecutive guanine residues were no longer present, while retaining the GC proportion of the complementary region (referred to as "stem" hereinbelow). The sequence of the non-complementary region (referred to as "loop" hereinbelow) was modified in such a way that Watson-Crick base pairing preferably would not be possible and no consecutive guanine residues would be present. As a result of modifying the loop, the CG motifs situated within this region were modified compared to 30L1. The model ODN constructed in this way will be referred to as KG hereinafter. The GL ODN corresponds to KG with a poly(G) sequence in the loop, which, in contrast to the one occurring in 30L1, is not situated within the CG motifs. The MS ODN corresponds to the starting molecule 30L1, but has additional guanine residues in the stem. The GS, GLS and ML ODNs include combinations of stem and loop of the above-described ODNs.

The molecules no30L1 and noGL, each having CG replaced by TG, were used as control molecules for the dependence of the observed effect of CG motifs.

The molecule dSLIM-60L1 was used as model molecule of a "dimeric" dSLIM-30L1, as might be formed by concatemerization. It consists of two partially complementary, yet non-self-complementary, ODNs (60L1forw and 60L1rev) which, following hybridization, have a 5' overhang to which another ODN (30L1-AGGG) with a corresponding 3' overhang and self-complementary 5' and 3' regions can be ligated. The sequences of the loops of the above 3 ODNs correspond to those of 30L1.

Fractions of dSLIM-30L1 obtained by separating a large quantity of dSLIM-30L1 using separation by means of a continuous NaCl gradient in a HPLC were provided by Melanie Rothe (Mologen AG).

The ODNs used in this work were purchased from TIB Molbiol (Berlin) with 5' phosphorylation (exceptions: M362, 2006), dissolved in $H_2O$ at a concentration of 3 g/l after HLC purification:

TABLE

ODNs used (phosphorothioate: small letters)

| Name and SEQ ID NO | Sequence | Structural features | Molecular weight (g/mol) |
|---|---|---|---|
| 30L1 (SEQ ID NO: 5) | CCT AGG GGT TAC CAC CTT CAT TGG AAA ACG TTC TTC GGG GCG TTC TTA GGT GGT AAC C | $G_4$ in stem and loop (S1, L1) | 17871 |
| KG (SEQ ID NO: 6) | CTG CAG CTG TAG CAG CTT CAT TCC ATA TCG TTC TTC GTG TCG TTC TTA GCT GCT ACA G | no poly(G) sequences, loop unpaired (S2, L2) | 17723 |
| ML (SEQ ID NO: 7) | CCT AGG GGT TAC CAC CTT CAT TCC ATA TCG TTC TTC GTG TCG TTC TTA GGT GGT AAC C | stem of 30L1, loop of KG (S1, L2) | 17723 |
| MS (SEQ ID NO: 8) | CCT AGG GGT GGG GGC CTT CAT TGG AAA ACG TTC TTC GGG GCG TTC TTA GGC CCC CAC C | 30L1 with additional $G_5$ in stem (S3, L1) | 17874 |
| GL (SEQ ID NO: 9) | CTG CAG CTG TAG CAG CTT CGG GGG GTA TCG TTC TTC GTG TCG TTC TTA GCT GCT ACA G | KG with $G_6$ in loop (S2, L3) | 17885 |
| GS (SEQ ID NO: 10) | CCT AGG GGT GGG GGC CTT CAT TCC ATA TCG TTC TTC GTG TCG TTC TTA GGC CCC CAC C | KG with stem of MS (S3, L2) | 17726 |
| GLS (SEQ ID NO: 11) | CCT AGG GGT GGG GGC CTT CGG GGG GTA TCG TTC TTC GTG TCG TTC TTA GGC CCC CAC C | stem of MS, loop of GL (S3, L3) | 17888 |

TABLE-continued

ODNs used (phosphorothioate: small letters)

| Name and SEQ ID NO | Sequence | Structural features | Molecular weight (g/mol) |
|---|---|---|---|
| no30L1 (SEQ ID NO: 12) | CCT AGG GGT TAC CAC CTT CAT TGG AAA ATG TTC TTT GGG GTG TTC TTA GGT GGT AAC C | 30L1 without CG motifs (TG instead of CG) | 17871 |
| noGL (SEQ ID NO: 13) | CTG CAG CTG TAG CAG CTT TGG GGG GTA TTG TTC TTTC GTG TTG TTC TTA GCT GCT ACA G | GL without CG motifs (TG instead of CG) | 17900 |
| 60L1 forw (SEQ ID NO: 14) | CCT AGG GGT TAC CAC CTT CAT TGG AAA ACG TTC TTC GGG GCG TTC TTT CCC CAA TGG TGG AA | non-self-complementary, loop of 30L1 | 19147 |
| 60L1 rev (SEQ ID NO: 15) | CCC CTT CCA CCA TTG GGG ATC ATT GGA AAA CGT TCT TCG GGG CGT TCT TAG GTG GTA ACC CC | non-self-complementary, loop of 30L1 | 19108 |
| 30L1-AGGG (SEQ ID NO: 16) | GGG GTT ACC ACC TTC ATT GGA AAA CGT TCT TCG GGG GCT TCT TAG GTG GTA A | self-complementary, 3' overhang | 16177 |
| M362 (SEQ ID NO: 17) | tcg tcg tcg ttc gaa cga cgt tga t | CpG-C phosphorothioate backbone | 7640 |
| 2006 (SEQ ID NO: 18) | tcg tcg ttt tgt cgt ttt gtc gtt | CpG-B phosphorothioate backbone | 7303 |

Owing to the orientation of its four H bridge binding sites, guanine is capable of forming a cyclic base quartet with 8 H bridges (G quartet) via guanine-guanine base pairing. A DNA sequence containing a number of consecutive guanine nucleotides is therefore capable of forming a tetrameric helical structure wherein the guanine bases show a high level of planarity with specific stacking interaction. Depending on the position, number and distribution of guanine nucleotides in the sequence, formation of various G structures is possible which can be divided into three groups: G2' DNA (bimolecular parallel or antiparallel tetraplexes), G4' DNA (unimolecular antiparallel tetraplexes) or G4 DNA (tetramolecular parallel tetraplexes). G4 DNA is capable of forming self-assembling nanostructures, so-called G wires. Apart from the number of available guanine residues and their arrangement and surrounding Watson-Crick base pairing, the formation and stability of G structures, the latter sometimes being very high, depends on the temperature, DNA concentration and the presence of various cations (e.g. $Na^+$, $K^+$, $Mg^{2+}$, $Ca^{2+}$). For example, G4 structures have been identified in telomer sequences, immunoglobulin switch regions and HIV DNA [Sen 1992, Marsh 1994, 1995].

Next, various monomeric and multimeric molecules containing combinations of various loop and stem sequences were produced. Three loop sequences and three stem sequences including long, short or no poly(G) motifs were used each time, thereby influencing the ability of forming G structures. Stable G structures can form under appropriate conditions in short ODNs (12mer) with only four consecutive guanine bases. In longer ODNs longer motifs are necessary because the probability of forming stable G structures positively correlates with the proportion of guanine bases contributing to the overall sequence [Sen, 1992].

Molecules having additional long poly(G) motifs show enhanced formation of multimeric molecules. Also, the elution profiles of these molecules are different from those having no long poly(G) motifs in that two peaks appear, the peak at higher elution volume corresponding to the DNA distribution encountered in the upper region of the agarose gels. The most remarkable change was observed for GL, the molecule whose poly(G) motifs are localized in the loop. Here, two distinctly separate peaks could be distinguished in the elution profile, where the peak at higher elution volume had a higher intensity than that at lower elution volume. For GL, the amount of DNA diffusely dispersed in the gel above the monomeric band was comparatively large, extending in its distribution to the pocket of the gel. These observations allow the conclusion that a relatively large amount of DNA is present in multimeric complexes. The distribution of the peaks in the HPLC elution profile and the distribution of the DNA following agarose gel electrophoresis were similar in the constructs containing poly(G) motifs in the stem (GS, MS). They showed a small second peak at higher elution volumes in the elution profile and a weakly visible, indiscrete distribution of DNA above the monomeric band in the agarose gel. Regarding the peak pattern (HPLC) and DNA distribution (agarose gel), the migration behavior in HPLC and agarose gel observed for molecules with poly(G) motifs in loop and stem (GLS) was between that of GL and GS and MS. Two separate peaks of equal height were observed in the elution profile, and the amount of DNA distributed in the upper region of the gel was somewhat higher than for molecules with poly(G) motifs in the stem (GS and MS), but lower than for GL. Accordingly, formation of multimeric molecules should be particularly favored when the poly(G) motifs are situated in the loop, as is the case with GL. The reason for this is lacking competition between formation of Watson-Crick base pairs and formation of G structures in a single-stranded loop. This precondition is also given in the GLS molecule. In this case, however, poly(G) motifs as possible partners of interaction are present both in the stem and loop. Hence, formation of intramolecular G2 structures, i.e., largely proceeding independently of the concentration, is possible. As a result, they represent a competition to intermolecular formation of G structures so that formation of higher-molecular weight complexes is reduced for GLS when compared to GL. The lowest tendency of forming higher-molecular weight complexes was observed in molecules with poly(G) motifs in the stem, although the poly(G) motifs in this case were longer than those in GL.

Given equal amounts of starting material, the above-described characteristics were not observed in the monomeric molecule 30L1 which, like GLS, has poly(G) motifs in stem and loop. The reason for this might be that, on the one hand, the poly(G) motifs in this molecule are shorter than those in the multimeric molecules. On the other hand, the structure prediction from "DNA mfold" indicates a higher tendency of forming Watson-Crick base pairs in the loop so that the probability of G structure formation should be further reduced. However, like the multimeric molecules with long poly(G) motifs, the fraction F4 obtained from a large amount of 30L1 by means of HPLC separation also shows the above-described diffuse DNA distribution in the upper region of the gel and remaining DNA in the gel pockets in polyacrylamide gel electrophoresis (see FIG. 10). Obviously, the proportion of higher-molecular weight complexes of G structures is so low for 30L1 that detection thereof is only possible when using higher amounts of starting material.

In contrast, the DNA shares in the pocket do not completely disappear for GL and GLS which have poly(G) motifs in the loop, and a regular, additional band pattern can be recognized. This is probably due to dimers or tetramers or non-degraded ODNs having remained in the aggregates, which have been dissolved from the aggregates by denaturation and are still bound to each other via guanine-guanine interaction.

The experimental properties show that the multimeric molecules with long poly(G) motifs are in fact formed by G structures. Apart from the appearance of an indiscrete DNA distribution in the upper gel region, said properties include the appearance of regular bands following denaturation, as is observed for GL and GLS in a polyacrylamide gel.

Figure 7:
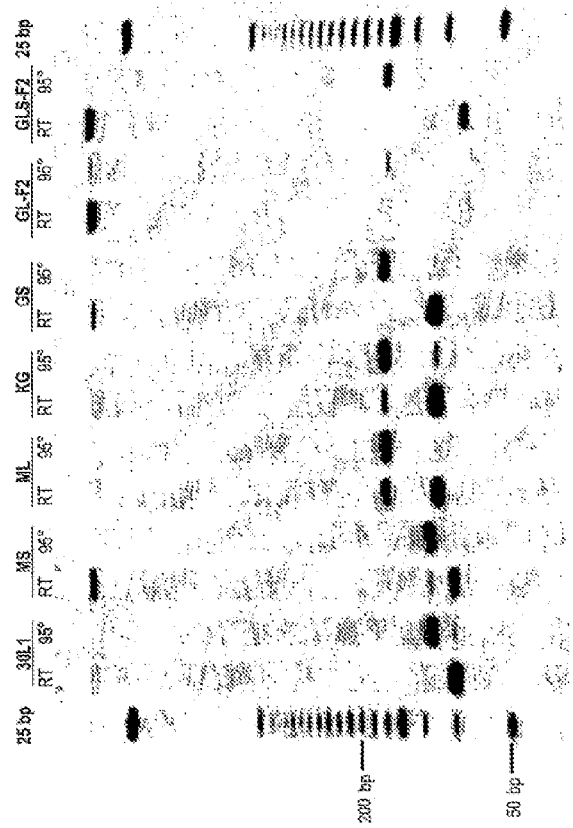
FIG. 7 shows thermal denaturation of various monomeric and multimeric dSLIM molecules.

In contrast to the band in the upper third of the gel, which was isolated from 30L1, the bands observed for KG and ML were no longer recognizable after denaturation (see FIG. 7). These bands are therefore dimers that are formed via base pair interactions between two monomeric molecules and, as a consequence, can easily be separated by means of thermal denaturation. The preferred appearance thereof in KG and ML might be due to their common loop sequence which favors interaction of two molecules.

HPLC fractionation of a large amount of 30L1 molecule furnished 4 fractions that showed highly different migration behavior in the gel. Concentrating the single fractions enabled separate dissolution thereof so that a number of bands previously unrecognizable in the gel became visible. The migration behavior of the first fraction corresponded to the two monomeric conformations observed, that of the second fraction corresponded to a continuous mixture of both conformations, where the open conformation prevailed after denaturation of this fraction, and that of the third fraction mainly corresponded to a dimeric molecule as described above. Having clearly visible shares of DNA that remained in the gel pocket, the fourth fraction was similar to MS in its migration behavior.

The shift of the band corresponding to a dimer for 30L1 and of the 30L1 fraction 3 in the cell culture medium compared to their migration distance in gel observed in water was remarkable. A comparison with Coomassie-stained gel shows that the corresponding band in medium runs at the same level with the lower protein band. Therefore, it can be assumed that shift of the band is caused by binding of the dimeric molecule to proteins.

The migration behavior of the bands corresponding to the monomer conformations was barely changed by addition of medium, it was only with GL that an increase of the band corresponding to the open conformation was observed. After incubation at 37° C. for five hours, a diffuse distribution of the DNA between the two bands previously observed was seen in KG and 30L1, where the intensity of the band corresponding to the open conformation decreased for KG. Under the selected conditions the open conformation is slightly favored compared to the aqueous solution. After 27 h of incubation in medium, the observed DNA intensities for ML and GL were massively reduced, and even with KG it was only the lower band that was visible with reduced intensity, while the smallest decrease in intensity was observed with 30L1. One possible explanation would be that the open conformations are more easily degraded than double-stranded conformations.

The immunostimulatory effect of various monomeric and multimeric molecules was to be investigated by determining the concentrations of IFN-γ, IFN-α and IL-6 in the supernatants of PBMC from human blood donations following stimulation with these molecules.

The test system used to determine the activity of the molecules using PBMC from human blood donations is a highly complex system wherein the different cells can influence each other via interaction and/or cytokine secretion so that assignment of an observed response to a particular cell type or reaction path is hardly possible. Moreover, there are great variations between the results of individual donors so that greater numbers of independent tests are required. The advantage of this test system is that it comes closest to the in vivo situation among all the possible well-established in vitro systems.

The tests showed that the detection of cell activation being used is subject to a relatively strong influence by the cell culturing conditions because IL-8/CXCL8 is also secreted in response to cell stress-inducing factors. In particular, this becomes evident in view of the results obtained with cells whose medium was not changed prior to stimulation (see FIG. 16) and wherein a high concentration of IL-8/CXCL8 was detected even in unstimulated cells. The determined ratio of the chemokine concentration measured in unstimulated cells and the chemokine concentration detected in stimulated cells was 1.3 and thus very low compared to cells where the medium had been changed. The latter had a ratio of 2.3. Therefore, to obtain results as informative as possible, culturing the cells under largely cell stress-free conditions is particularly important in this test. Presumably, cell stress is the reason why the results obtained with cells stimulated 24 h after seeding were not as clear as those obtained with cells grown to confluence. Passaging of cells and associated cell culturing techniques generate high cell stress.

As observed in the test relating to dependence on the stimulation time (see FIG. 17), a difference in the secreted amount of chemokines between unstimulated and stimulated cells could be detected after only 6 hours. The amount of IL-8/CXCL8 increased between 6 h and 24 h, while the increase observed from 24 h to 48 h was small.

The activities of the molecules in the test system were investigated in two tests where differences between the individual molecules employed were observed (see FIG. 18).

The highest secretion of IL-8/CXCL8 in the tests was induced by stimulation with GL, which was somewhat higher than that induced by ODN 2006. The amounts of IL-8/CXCL8 measured following stimulation with KG and 30L1 were somewhat lower, where KG showed a somewhat higher activity compared to 30L1. The observed differences in activity of these different monomeric and multimeric molecules might be due to the observed structural differences. Thus, it is possible to demonstrate that KG and GL, as compared to 30L1, tend to have an open conformation of the loop region with CG motifs, so that the single-stranded form thereof is preferred. As shown by Rutz et al. by means of surface plasmon resonance, single-stranded DNA binds to TLR9 with higher affinity than double-stranded DNA [Rutz, 2004], which might be the reason for the somewhat higher activity of KG and GL compared to 30L1. However, the CG motifs are different even in 30L1 and KG/GL so that the different activity might also be due to the different affinity of the different CG motifs to the receptor.

GL, the molecule with the highest potency of forming aggregates, showed the highest activity among the tested molecules in both tests, which is possibly due to stronger crosslinking of the receptors by the higher-molecular weight complexes. However, enhanced activity of GL in the tests performed with PBMC was not observed. On the other hand, it might be possible that other pattern recognition receptors present in the more complex system of PBMC are involved in the immunomodulatory activity of monomeric and multimeric molecules that is observed therein, which recognize other structural features of the molecules. Thus, for example, it might be possible that recognition also proceeds via other nucleic acid-specific receptors such as TLR8 or TLR7, thereby producing a cooperative or modulating effect.

In conclusion, it can be stated that specifically the presence of poly(G) motifs in the loop of the monomeric molecules favors the formation of multimeric complexes. In addition, these complexes have high stability to thermal denaturation.

To identify the differences of the immunomodulatory effect of various constructs, the latter were employed in stimulation experiments with PBMC.

The results show that the multimeric molecules have particularly high activity.

Determination of DNA Concentration

The concentration of the ODNs and monomeric DNA molecules was determined by measuring the absorption at 260 nm ($A_{260}$). It is the aromatic rings of the nucleic acid bases that are responsible for the absorption at 260 nm, the individual bases having different molar absorption coefficients ε (A>G>T>C). As a result of chromophore-chromophore interactions, double-stranded nucleic acids have a lower absorption than single-stranded nucleic acids (hypochromic effect).

To determine the concentration, the corresponding volume of DNA solution to be determined was initially diluted in an Eppendorf vessel with TE buffer in a final volume of 300 μl (ODN 1:200, dSLIM 1:100). The DNA solution was subsequently transferred into a quartz cuvette, and the absorption at 260 nm was measured in a photometer versus TE buffer. The concentration was calculated from the measured absorption according to the equation:

$$c(\mu g/ml) = A_{260} \times \text{dilution factor} \times \text{conversion factor}$$

The conversion factor is an approximate value and is estimated to be 50 μg/ml for double-stranded DNA and 33 μg/ml for single-stranded DNA. Due to the share of double-stranded regions in ODN and monomeric DNA molecules, a standardized conversion factor of 50 μg/ml is used. Double determinations with separate dilutions were performed each time, from which the mean value was calculated.

Preparation of Monomeric DNA Molecules

For the preparation of the monomeric DNA molecules, sterile (disposable) materials and fresh buffers or sterile-filtrated buffers stored at −20° C. were used so as to avoid contamination with bacteria, because the stimulation results can be falsified even by small quantities of endotoxins.

The first step in the production of monomeric DNA molecules is ligation of two ODNs using T4 DNA ligase. T4 DNA ligase catalyzes formation of a phosphodiester bond between 5'-phosphate and 3'-OH ends in double-stranded DNA or RNA with blunt or cohesive ends. In addition, it is capable of repairing single-strand breaks in double-stranded DNA, RNA or DNA-RNA hybrids.

Ligation of two ODNs proceeds between the 5'-phosphate overhang of one ODN and the 3' end of the other ODN, thereby forming a circular molecule. The reaction likewise produces the multimeric DNA molecules according to the invention.

The ODN starting amount for the preparation of the molecules was 500 to 1000 μg. For ligation, the ODNs were employed at a concentration of 0.55 g/l in 1× ligase buffer. To this end, they were diluted with Aqua rinse and the corresponding amount of 10× ligase buffer was added. Following thorough mixing, T4 DNA ligase was added in such an amount that a ratio of 0.01 U/μg DNA was present. The ligation batch was incubated in a water bath at 37° C. for 15 to 24 h.

T7 digestion was used to degrade non-ligated ODNs. T7 DNA polymerase is a template-dependent DNA polymerase which catalyzes the DNA synthesis in 5'-3' direction but also has 3'-5' exonuclease activity on single- and double-stranded DNA, thus being suitable for the degradation of non-ligated ODNs.

The success of ligation was examined prior to performing the T7 digestion. To this end, 0.3 μg of ODNs, ligation batch and a test T7 digestion each time were separated on a 3% agarose gel (see 2.4.1). For the test T7 digestion, excess T7 DNA polymerase at a ratio of 10 U/1.1 μg of DNA was employed in a volume of 21 μl. The reaction proceeded for 1 h at 37° C. and was terminated by heating to 70° C. for 10 minutes.

For T7 digestion, the ligation batch was diluted with Aqua rinse and a corresponding amount of 10× ligase buffer so that the DNA was present at a concentration of 0.3 g/l in 1× ligase buffer. The amount of T7 DNA polymerase required to make a ratio of 0.03 U/μg DNA was added. The batch was incubated in a water bath at 37° C. for 15 to 24 h. The success of the reaction was examined by separating 0.3 μg of ligation batch along with 0.3 μg and 0.9 μg of the T7 digestion batch on a 3% agarose gel.

Purification of the Molecules According to the Invention

Purification was effected using anion exchange chromatography. The principle of this method is based on the presence of positively charged groups in a porous matrix (stationary phase), which interact with nucleic acid phosphate groups negatively charged above pH 2 so that the latter are bound to the stationary phase. The strength of the interaction depends on the pH value, the ionic strength of the mobile phase and the negative charges present in the molecule. Uncharged molecules give no or only weak interaction with the stationary phase and are rapidly eluted with a mobile phase of low ionic strength. By increasing the ionic strength of the mobile phase, the molecules bound to the stationary phase are displaced from the column. As a result of stronger interaction with the stationary phase, larger nucleic acids are eluted later than smaller ones [Lottspeich, 1998; Mülhardt, 2003].

Fractogel-DMAE, a polymer resin with dimethylaminoethyl groups, was used as stationary phase in purification. An NaCl step-by-step gradient (0%, 50%, 100% 1 M NaCl) was used for separation.

Prior to starting the purification, all outlets and inlets of the HPLC apparatus, filled with 20% ethanol when not in operation, are initially rinsed with Aqua rinse, and the column is packed. To this end, 1.6-1.8 ml of DMAE was placed in the column, filled with water up to the edge, and the column was wagged to ensure uniform distribution. Subsequently, the column was connected to the HPLC apparatus in an air bubble-free manner. The column was rinsed at a flow rate of 1 ml/min until the column material had completely settled. The upper piston was screwed on the matrix in an air bubble-free manner, and excess water was displaced from the column. The column was reconnected to the HPLC apparatus and rinsed at a flow rate of 1 ml/min, and possibly occurring dead spaces between matrix and piston were eliminated by repeating the last step. The column thus packed, as well as the entire HPLC apparatus, were subsequently equilibrated with T20 buffer at a flow rate of 1 ml/min. Equilibration of the column was effected using an approximately 10fold column matrix volume and checked using a pH indicator strip. Using a Hamilton syringe, the batches were injected into the HPLC apparatus via a 2 ml sample loop. The HPLC apparatus was controlled by means of a software protocol designed to effect automatic fractionation. In some cases, however, side-peaks that occurred were fractionated by hand. Prior to sample application, the column was equilibrated with the double column volume (CV), and then elution of unbound molecules (proteins, nucleotides) was effected with 5 CV of T20 buffer, followed by elution of weakly bound molecules (ATP, ODN) with 7 CV of 50% T20N1000 buffer and elution of dSLIM with 7 CV of 100% T20N1000 buffer. The flow rate was 1 ml/min. Thereafter, the column was re-equilibrated with 10 CV of T20 buffer for the next sample application, and the outlets and inlets of the HPLC apparatus were manually rinsed with T20 buffer.

The HPLC-purified molecules were concentrated using ethanol precipitation and desalted. In the presence of monovalent cations, nucleic acids in alcohol form an insoluble precipitate which can be isolated by centrifugation. Co-precipitated salt can largely be removed by washing in 70% ethanol because, unlike nucleic acids, it is soluble therein. To increase the yield in case of smaller amounts of nucleic acids less prone to precipitation, it is possible to perform the precipitation at low temperatures and/or add $Mg^{2+}$ ions. If not interfering with subsequent uses, carrier materials such as tRNA or glycogen can also be added, which increase the effective concentration of the nucleic acids [Lottspeich, 1998; Mülhardt, 2003].

For precipitation, the respective fractions of the HPLC purification were transferred into Corex centrifuge glassware and added with 1/100 volume of 1 M $MgCl_2$, 1/10 volume of 3 M sodium acetate solution and 2.5 volumes of 96% ethanol. The batches were mixed and precipitated at 20° C. for 2-24 h. The batches were subsequently centrifuged at 10,000 rpm (11,000 g) and 4° C. for 30 min, the supernatant was removed, washed with 5 ml 70% ethanol and centrifuged for another 10-30 min at 10,000 rpm (11,000 g) and 4° C. The supernatant was removed and the DNA pellet was dried on air until the odor of alcohol had disappeared. The DNA was taken up in 100-350 μl of Aqua rinse and transferred into sterile 1.5 ml reaction vessels. The volume for resuspension was estimated with reference to the amount of DNA employed in the preparation so that a concentration of 1 g/l with a yield of 50% was obtained.

Agarose Gel Electrophoresis

For separation and characterization of nucleic acids, gel electrophoresis is a suitable means. The nucleic acids, being negatively charged over a wide pH range, are exposed to an electric field in a matrix of agarose or polyacrylamide and migrate to the anode. Their migration rate varies depending on their size. The behavior of nucleic acids (up to about 10 kb) during gel electrophoresis can be described using a combination of two theories. The Ogstron screening effect is based on the assumption that nucleic acids assume a globular shape and collide with the gel matrix more frequently the greater the circumference of the particle, so that larger molecules are slowed down more strongly than small ones. According to this theory, molecules whose diameter is greater than the pore diameter of the gel should not migrate through the gel. The reptation theory assumes that nucleic acids lose their globular form in the gel and move through the gel in a snake-like fashion with one end ahead, which movement requires more time for longer molecules than for short ones. Due to the influence of size on the migration rate of nucleic acids, the formation of secondary structures has an effect on the migration behavior in the gel. Thus, for example, the migration behavior of plasmid DNA varies according to the conformation thereof. The migration rate increases from open (form I) via linear (form III), superhelical (form II) to denatured (coiled) plasmid DNA. For linear double-stranded DNA (form III), a correlation between $\log_{10}$, length (in bp) and relative migration distance in the gel exists over a wide range so that relatively precise size determination is possible based on length standards.

Detection of nucleic acids in gels can be effected using ethidium bromide which, owing to its planar structure, is intercalated in the DNA, so that fluorescence excitation with light in the UV region (254-366 nm) is possible, the emission of which is observed in the orange-red region (590 nm) [Lottspeich, 1998].

Agarose is a polysaccharide which is recovered from marine algae and forms gels with relatively large pores in aqueous solution after cooling (1% (w/v) about 150 nm). The pore size is inversely proportional to the agarose concentration. Agarose gels are suitable for the separation of nucleic acids of 0.1 to 25 kb in length. The advantage of agarose gels lies in their relatively large separation range and easy handling. However, the resolution for small DNA fragments is very low. Suitable for the separation of smaller DNA fragments is Sieve Agarose, a derivatized form of agarose [Lottspeich, 1998; Mühlhardt, 2003].

To separate the ODNs and molecules according to the invention, 3% agarose gel in 1×TAE buffer with 0.125 µg/ml ethidium bromide was used. Using the BioRad system, horizontal gels were cast (40 ml for small gels with 8 pockets, 100 ml for large gels with 20 pockets). The samples to be analyzed were applied in 1× test buffer along with appropriate length standards (see 2.4.3). Electrophoresis was performed in 1×TAE buffer at 120 V for 30 min. The gels were photographed using gel documentation equipment.

Native Polyacrylamide Gel Electrophoresis (PAGE)

Polyacrylamide gels are formed by free-radical copolymerization of acrylamide monomers using the crosslinker N,N'-methylenebisacrylamide. The pore size of the gels ranges from about 3-6 nm and depends on the total acrylamide concentration (% T=$m_{acrylamide}$+$m_{bisacrylamide}$ (w/v)) and the degree of crosslinking (% C=$m_{bisacrylamide}$/$m_{acrylamide}$+$m_{bisacrylamide}$). It decreases with increasing T at constant C and has a minimum at 5% C at constant T. Polyacrylamide gels have very good resolution power especially for small DNA fragments (<1 kb). However, the separation range is substantially narrower compared to agarose gels. The separation range can be made broader by using gradient gels. The superior resolution power of polyacrylamide gels enables differentiation of different DNA conformations which, due to their different forms, have different migration behavior which can be influenced via temperature and ion concentration.

Gels with 8% T, 2.6% C were found optimal for the separation of the molecules, and gels with 12% T, 5% C in 1×TBE for the separation of ODNs. The horizontal gels were cast on the day before electrophoresis (15 ml/gel$_{small}$, 25 ml/gel$_{large}$) and stored in a refrigerator overnight. Prior to sample application, the gels were subjected to pre-electrophoresis at 70 V (170 $V_{large}$) until changes in the current strength were no longer observed (10-11 mA). The samples were applied in 1× test buffer along with appropriate length standards (see 2.4.3) without addition of dyes. To monitor the progress of electrophoresis, 1× Loading Dye was applied in a separate lane. Electrophoresis was performed in 1×TBE at a constant voltage of 70 V (170 $V_{large}$) (≈9 V/cm) and room temperature and was terminated as soon as bromophenol blue had reached the bottom end of the gel (about 2 h). After electrophoresis the gels were stained in ethidium bromide solution for 10-15 min and photographed using the gel documentation equipment. In the event of excessive background staining, the gels were washed in demineralized water for 10-30 min.

Thermal Denaturation and Renaturation for Band Assignment

Since monomeric DNA molecules are circular DNA molecules which, much like plasmid DNA, show a complex migration behavior in a gel, assignment of bands observed in the gel to a particular conformation or size is not a straightforward matter. The fact that differing conformations, in contrast to molecules of different size, can be reversibly interconverted under suitable conditions can be used in differentiation.

Different conformations have a different degree of compaction and therefore should be discernable in the gel by their differing migration behavior, with compact DNA forms frequently having higher mobility in the gel compared to more voluminous, open DNA forms. The compact forms should be convertible into the open forms by destroying hydrogen bridges.

To make an assignment of the bands observed in the polyacrylamide gel, the molecules were thermally denatured by heating to 95° C. for 10 minutes. The denatured samples were immediately placed on ice to prevent renaturation. To this end, a mastermix was produced which included the respective dSLIM molecule at a concentration of 0.05 g/l in 1×TE buffer. The batch was divided in half and 1 batch was heated and 1 batch was kept at room temperature. Samples to be applied on gel were taken from the batches, added with the corresponding amount of 5× sample buffer and separated on a native 8% polyacrylamide gel. To observe renaturation, the remaining denatured batch was divided once more and subsequently incubated for 3 days at 4° C. and 37° C., respectively. The remaining non-denatured batch was stored at 4° C. and likewise divided after 3 days, and one part was denatured as described above and the other part was kept at room temperature. The batches were added with the corresponding amount of 5× sample buffer and separated on a native 8% polyacrylamide gel.

Incubation in Cell Culture Medium

The activity of the molecules was tested in vitro using PBMC and HEK293 cells. The molecules were dissolved in protein-containing cell culture medium rather than buffer and incubated at a temperature of 37° C. The intention therefore was to investigate the influence of these modified parameters on the structure and stability of the molecules and ODNs.

One important factor that may influence the activity of DNA molecules in various ways is non-specific binding to proteins. Binding to proteins changes the migration behavior of DNA in a non-denaturing polyacrylamide gel electrophoresis (native PAGE) so that a shift of the DNA band in the presence of protein can be recognized. In most cases the electrophoretic mobility of a DNA-protein complex is reduced compared to DNA; for DNA minicircles, the electrophoretic mobility may also be increased if the degree of compacting is increased by protein binding [Toulmé, 1995].

To investigate the molecules and ODNs employed in the stimulation tests in terms of their behavior under conditions encountered in the stimulation tests, the ODN and molecule solutions were diluted to a concentration of 1 µM in medium and incubated for 5 h or 24 h at 37° C. on a hotstage or, following addition of an appropriate amount of 5× sample buffer, directly separated on a polyacrylamide gel. ODN and molecule solutions correspondingly diluted in $H_2O$ were applied for comparison. To verify that the observed changes had been caused by the presence of proteins, batches including ODN and molecules of the invention were diluted to a concentration of 1 µM in medium to which no FCS had been added. To compare the migration distances of DNA and protein bands in the gel, thus allowing conclusions as to possible protein binding, DNA as well as proteins were detected in the gels.

The additional detection of proteins was performed following nucleic acid detection. The gels were fixed for 30 min in fixing solution and subsequently stained for 30-60 min in Coomassie solution. Excess dye was removed by incubation in destaining solution overnight, and the gels were photographed using the gel documentation equipment.

DNA Length Standards Used:

As to the length standards, the amount/mm pocket width recommended by the supplier was applied in 1× sample buffer each time. The following standards were used:

GeneRuler 100 bp DNA Ladder Plus (MBI Fermentas)
GeneRuler 50 bp DNA Ladder (MBI Fermentas)
10 bp DNA Ladder (Invitrogen)
25 bp DNA Ladder (Invitrogen)

Cell Culture

All cell culture operations were performed under sterile conditions using sterile disposable materials.

The conditions in the incubator were 37° C., 5% $CO_2$, 90% humidity.

Investigation of the Immunomodulatory Effect of the Molecules in PBMC

To investigate the immunomodulatory effect of the multimeric molecules, the cytokine secretion of lymphocytes and monocytes recovered from human blood donations was measured using ELISA.

The starting material for the isolation of lymphocytes and monocytes, also referred to as peripheral blood mononuclear cells (PBMC)=mononuclear cell fraction of the peripheral blood, was a leukocyte concentrate, also referred to as buffy coat, which is obtained by centrifugation of whole blood and was purchased from the DRK-Blutspendedienst Berlin Wannsee. Using Ficoll-Hypaque density gradient centrifugation, the PBMC can be separated from other components of the leukocyte concentrate (plasma, thrombocytes, erythrocytes, granulocytes). The Ficoll-Hypaque separation medium is a solution including a mixture of Ficoll 400, a strongly branched polymer of saccharose monomers cross-linked via epichlorohydrin and sodium diatrizoate (Hypaque) with a density of 1.077 g/ml. Using isopyknic centrifugation of the separation medium with a layer of dilute leukocyte concentrate on top, it is possible to separate the different components according to the different density thereof, thus obtaining the fractions represented in FIG. 1 [Luttmann, 2004].

To isolate PBMC, each leukocyte concentrate was transferred into a sterile 250 ml bottle and diluted 1:2 with PBS. 15 ml of Ficoll-Hypaque solution each time was placed in four 50 ml centrifuge tubes, carefully overlayered with about 30 ml of blood-PBS mixture using a 10 ml pipette and centrifuged at 800 g for 20 min with the brake turned off (total time about 50 min) The PBMC-containing interphase was carefully sucked off with a 5 ml pipette and transferred into 50 ml centrifuge tubes with 20 ml of cold PBS. To remove contaminations of erythrocytes, Ficoll/Hypaque and thrombocytes, the cells were subsequently subjected to a number of wash steps. While all steps up to the isolation of PBMC were carried out at room temperature so as to avoid aggregation of thrombocytes, the wash steps were carried out at 4° C. to prevent adhesion of monocytes to the plastic materials employed and thus loss thereof. In the first wash step the cells were centrifuged at 400 g for 8 min at 4° C. The supernatant was sucked off and the cell pellet was resuspended in 5 ml of cold PBS and filled up to 45 ml with cold PBS. The following wash steps were carried out in the same manner, but centrifugation proceeded at 300 g for 5 min. The wash steps were repeated until the supernatant was clear and the pellet had a yellow color (about 5-6 times). The cells were subsequently resuspended in 5 ml of cold medium each time and combined, and the volume was filled up with cold medium to make 30 ml. The cell number was determined using an automatic cell counter at an exclusion size of 8 µm and adjusted to a concentration of $4 \times 10^6$ cells/ml using cold medium.

600 µl of previously isolated PBMC at a concentration of $4 \times 10^6$ cells/ml was placed in each well of 24-well cell culture plates. Thereafter, the corresponding volume of molecules to be tested was added so that the concentration in the batch was 1 µM. The cells were incubated for 2 days (42-48 h) in an incubator. The cell suspension was transferred into an Eppendorf reaction vessel and centrifuged in a Biofuge at 3000 rpm for 4 min. The cell-free supernatants thus obtained were transferred into a new reaction vessel and either directly used to determine the cytokine concentration by means of ELISA or stored at −70° C.

Culturing of HEK293 Cells

The cells were cultured in 162 $cm^2$ cell culture bottles. They were seeded at a density of $1.3-1.9 \times 10^5$ cells/$cm^2$. Following incubation in an incubator for 2-3 days, the cells were divided 1:3. To this end, the medium was sucked off, the cells were washed with 10 ml PBS and subsequently incubated at room temperature for 3-5 min, followed by detaching with 5 ml of trypsin/EDTA solution. The reaction was terminated by adding 5 ml of medium. The cells were resuspended and another 5 ml of medium was added. 5 ml of cell suspension each time was either kept in the cell culture bottle or transferred into a new one and added with 45 ml of medium. Occasionally, some cells detached from the bottom of the bottle before the medium had been sucked off. In this event, the cells were transferred into a sterile centrifuge tube and centrifuged at 300 g for 4 min. Thereafter, the medium was sucked off and the cells were resuspended in 5 ml of trypsin/EDTA solution, added with 10 ml of medium and transferred into a new cell culture bottle as described above.

Stimulation of HEK293 Cells

To establish the test, HEK293-TLR9 and HEK293 null cells at a concentration of $0.6-1 \times 10^6$ cells/ml each time were seeded in a volume of 400 µl in 24-well cell culture plates and cultured for 1-5 days. The cell number was determined using the cell counter at an exclusion size of 8 µm, and the appropriate concentration was adjusted. For long-term culturing, the medium was changed after 48 h. To this end, the medium was carefully sucked off and 400 µl of fresh medium each time was carefully added to the cells. Also, in some batches the medium was changed immediately prior to the addition of stimulants. Stimulation was effected by adding an appropriate volume of ODNs/molecules so as to reach a final concentration of 2.5 µM and 1 µM, respectively. LPS was employed at a concentration of 0.5 µg/ml. Thereafter, the cells were incubated in an incubator for varying periods of time (6-48 h). Finally, the medium was transferred into 1.5 ml reaction vessels, centrifuged in the Biofuge at 1400 rpm to pelletize cells possibly included, and the supernatants were used to determine the IL-8 concentration by means of ELISA.

Cytokine/Chemokine Detection Using ELISA

To investigate the immunomodulatory effect of dSLIM on PBMC, the induction of IL-6, IFN-α alpha and IFN-γ was measured.

IL-6 is a multifunctional cytokine which is secreted by a variety of activated lymphocytes and monocytes and, apart from inducing acute-phase proteins in hepatocytes, has a promoting effect on the growth, differentiation and phagocytosis of lymphocytes [Kirchner, 1994].

IFN-α, which has several subtypes, pertains to the family of type I interferons mainly having an antiviral effect. Large amounts of IFN are secreted by pDC following activation of TLR7, 8 or 9 [Perry, 2005], see also section 1.3.2.

IFN-γ is secreted predominantly by NK and T cells but also by monocytes, dendritic cells and B cells. It is the only type II interferon and, in contrast to type I interferons, rather has an immunomodulatory than an antiviral effect. Apart from its role in differentiation, IFN-γ is the most important effector cytokine of a $T_H1$-directed immune response.

Secretion of IL8/CXCL8 was used to detect activation of TLR9 in transformed HEK293 cells. IL-8 is a CXC chemokine secreted by leukocytes but also by fibroblasts, endothelial and epithelial cells. The induction of IL8/CXCL8 proceeds e.g. via IL-1 and TNF-γ but also via PRR and environmental factors such as hypoxia. The expression of IL8/CXCL8 is regulated by regulation of transcription via cooperative activation of NF-α and AP-1 and on the level of mRNA stability. Apart from its effect as activator of neutrophils, IL8/CXCL8 has a chemotactic effect on various leukocytes and is involved in the process of transmigration of leukocytes in tissues [Mukaida, 2003].

To detect cytokines in the cell culture supernatants of PBMC and HEK293 cells, the enzyme-linked immunosorbent assay (ELISA) was used in the form of a "sandwich ELISA". It is a quantitative immunoassay wherein specific antibodies for the protein to be detected are immobilized on the surface of a microtiter plate by adsorption. Binding of the antigen to the respective antibody likewise immobilized the former, and other components can be removed by washing. Binding of antigen and antibody is an equilibrium reaction so that the amount of bound antigen is concentration-dependent. Detection of the antigen is effected using a second specific, biotinylated antibody which in turn binds to the streptavidin-conjugated enzyme used in detection. In the assay performed herein the enzyme was horseradish peroxidase (HRP). The actual measured quantity is the amount (concentration) of a chromogenic substrate reacted by the enzyme within a defined period of time. The substrate used herein was TMB (3,3',5,5'-tetramethylbenzidine) which is oxidized in the presence of $H_2O_2$ to absorb light of a wavelength of 370 nm (blue). The reaction is terminated by addition of $H_2SO_4$, thereby changing the wavelength of absorption to 450 nm (yellow) [Luttmann, 2004]. Using a standard dilution series of known concentration of cytokine to be determined, it is possible in this way to determine unknown cytokine concentrations in the cell culture supernatants.

The required antibody pairs, standard, enzyme and substrate solutions were purchased from R&D Systems in the form of kits. The equipment and materials for implementation are presented in the table below.

IL-6 and IFN-γ

Detection of IL-6 and IFN-γ in the cell culture supernatants of PBMC was performed using the DuoSet ELISA Development System Kits from R&D Systems according to the enclosed instructions. To this end, the "capture antibody" was diluted with PBS to a concentration of 4 µg/ml (IFN-γ) and 2 µg/ml (IL-6), respectively, and 100 µl each time was placed in the wells of a microtiter plate. The plate was incubated at room temperature overnight, subsequently washed 3 times with wash buffer and incubated with 300 µl of blocking buffer per well for 1-2 h to saturate free binding sites. The plate was washed 3 times with wash buffer, and 100 µl of samples and standards each time were subsequently placed on the plate. The supernatants were used at a dilution of 1:2 in reagent buffer for IL-6 detection and undiluted for IFN-γ detection. The standard dilution series for IL-6 comprised the following concentrations: 12.5; 25; 50; 100; 200; 350; 700 µg/ml. The standard dilution series for IFN-γ comprised the following concentrations: 12.5; 25; 50; 100; 250; 500; 1000 µg/ml. Double determinations were performed in each case. The incubation time was 2 h. After washing 3 times with wash buffer, 100 µl of "detection antibody" at a concentration of 100 ng/ml (IL-6) and 200 ng/ml (IFN-γ), respectively, in reagent buffer was placed on the plate each time. After an incubation time of 2 h, the plate was washed 3 times with wash buffer, and 100 µl of streptavidin-HRP diluted 1:200 in reagent buffer was placed in each well. The incubation time was 20 min. Following a final triple wash step, 100 µl of substrate solution ("color reagent" A and B at a ratio of 1:1) each time was added to the plates and incubated for 20 min in the dark. The reaction was terminated by adding 50 µl of 1 M $H_2SO_4$, and the absorption in each single well was measured at 450 nm in a microplate reader. Assessment was performed using the software SoftMax Pro 2.6. The standard curve was calculated with a 4-parameter fit.

IFN-α

Detection of IFN-α in the cell culture supernatants of PBMC was performed using the Human Interferon-α ELISA Kit from Biosource according to the enclosed instructions. 100 µl of standards and samples per well were added to the microtiter strips included in the kit, already provided with antibodies and blocked, and incubated for 1 h at RT. The supernatants were used diluted 1:2 with dilution buffer, and the standard dilution series comprised the following concentrations: 156; 312; 625; 1250; 2500; 5000 µg/ml. Following a wash step, 100 µl of Antibody Concentrate D in Dilution Buffer C was added to each well and incubated for 1 h at RT. The plate was washed 3 times and 100 µl of HRP in HRP Diluent was added with to each plate and incubated for 1 h. The solution was removed by washing 4 times and 100 µl of Substrate Solution G was pipetted in each well. This was incubated in the dark for 20 min, and the reaction was terminated by addition of 100 µl of Stop Solution H. The absorption at 450 nm was measured in the microplate reader. Assessment was performed using the software SoftMax Pro 2.6. The standard curve was calculated with a point-to-point fit.

IL-8/CXCL8

Detection of IL-8/CXCL8 in the cell culture supernatants of HEK293 cells was performed using the DuoSet ELISA Development System Kit from R&D Systems according to the enclosed instructions and was identical to that described for IL-6 and IFN-γ. The standard dilution series comprised the following concentrations: 31.25; 62.5; 125; 250; 500; 1000; 2000 µg/ml. The supernatants were employed in undiluted form. The antibody concentrations employed were: capture antibody 4 µg/ml, detection antibody 20 ng/ml.

Preparation and Description of Multimeric DNA Molecules

To investigate the influence of structural features, particularly those favoring the capability of forming G structures, combinations of monomeric DNA molecules with poly(G) motifs in various regions were produced using the method according to the invention which, apart from lyophilization, is in accordance with that of monomer preparation. To this end, three different sequences for stem (S) and loop (L) each time were combined which, on the one hand, differed in the number and localization of guanine bases, but also in the loop secondary structure predicted by the "DNA mfold" program. The individual sequences and their structural features are represented in the following table:

TABLE 3.1

Structural features and sequences L1-L3, S1-S3 (red: poly(G))

| Name and SEQ ID NO | Sequence | Poly(G) sequence | Structural features Loop tend. open |
|---|---|---|---|
| L1 (SEQ ID NO: 19) | T CAT TGG AAA ACG TTC TTC GGG GCG TTC TT | short ($G_4$) within CG motif | no |
| L2 (SEQ ID NO: 20) | T CAT TCC ATA TCG TTC TTC GTG TCG TTC TT | none | yes |
| L3 (SEQ ID NO: 21) | T CGG GGG GTA TCG TTC TTC GTG TCG TTC TT | long ($G_6$) outside CG motif | yes |
| S1 (SEQ ID NO: 22; SEQ ID NO: 23) | 5'-CCT AGG GGT TAC CAC CT . . . 3'- CCA ATG GTG GA . . . | short | |
| S2 (SEQ ID NO: 24; SEQ ID NO: 25) | 5'-CTG CAG CTG TAG CAG CT . . . 3'-GAC ATC GTC GA . . . | none | |
| S3 (SEQ ID NO: 26; SEQ ID NO: 27) | 5'-CCT AGG GGT GGG GGC CT . . . 3'-CCA CCC CCG GA . . . | long ($G_4TG_5$) | |

The following diagram gives an overview of combinations used and their nomenclature used hereinbelow:

TABLE 3.2

Nomenclature of molecules with different loop/stem combinations

|  | S1 | S2 | S3 |
|---|---|---|---|
| L1 | 30L1 | — | MS |
| L2 | ML | KG | GS |
| L3 | — | GL | GLS |

As demonstrated above, the polymeric dSLIM molecules which, in the meaning of the invention, can also be referred to as multimeric molecules or oligomeric molecules, are very well suited to induce an enhanced immune response in an organism. The enhanced immune response enabled advantageous use of the agents in connection with chemotherapeutic agents. Compared to the additive effect of the two agents, the combination of chemotherapeutic agents and agents according to the invention results in a synergistic effect in the treatment of tumors. Owing to the combination with the agent according to the invention, which can be obtained by means of the process steps mentioned above (see main claim), all effects of the additionally employed chemotherapeutic or cytostatic agents are enhanced. Although monomeric forms of dSLIM molecules have already been combined with chemotherapeutic or cytostatic agents, the effect achieved by combining the multimeric or polymeric form of dSLIM with cytostatic agents was a complete surprise. In practical use of a combination agent comprising the monomeric form of dSLIM and the cytostatic agents it was found that only particular properties of cytostatic agents could be improved but not—as with the polymeric form—their overall properties. Also, activation of the immune system by the polymeric/multimeric form of dSLIM was surprisingly higher so that an overall result in the treatment of tumors could be achieved that was surprisingly improved compared to the use of the monomeric form of cytostatic agents. Thus, in particular, formation of metastases was prevented through the use of multimeric dSLIM molecules in an organism when administering cytostatic agents/chemotherapeutic agents together with these agents. Combining in the meaning of the invention is understood to be simultaneous as well as time-shifted administration of both agents.

Figure 2:
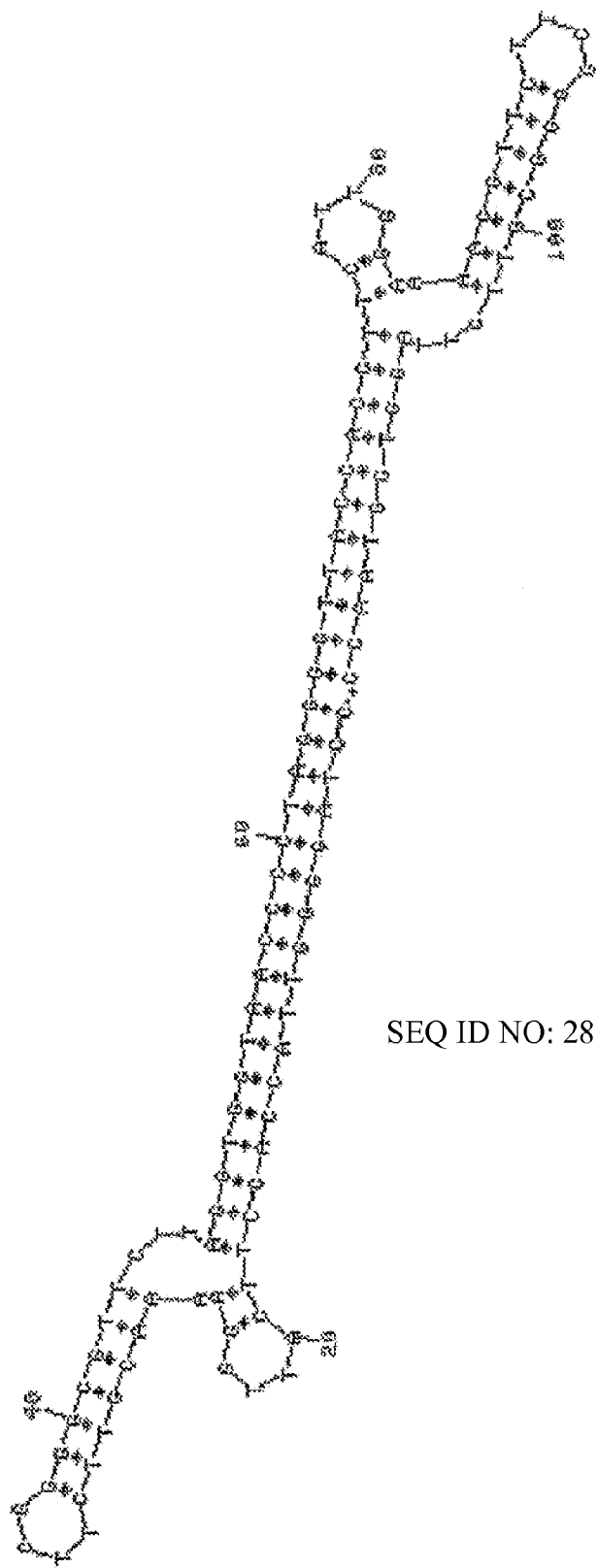
FIGS. 2 and 3 exemplify the two different secondary structures of the dSLIM molecules 30L1 (FIG. 2, SEQ ID NO: 28) (such as MS) and KG (FIG. 3, SEQ ID NO: 29) (such as ML, GS, GL, GLS) for the three loop sequences as calculated by "DNA mfold" (Conditions: 150 mM NaCl, 0.5 mM $MgCl_2$ and 37° C.). In contrast to 30L1, no base pairings in the loop were predicted for KG under the conditions selected.
Figure 3:
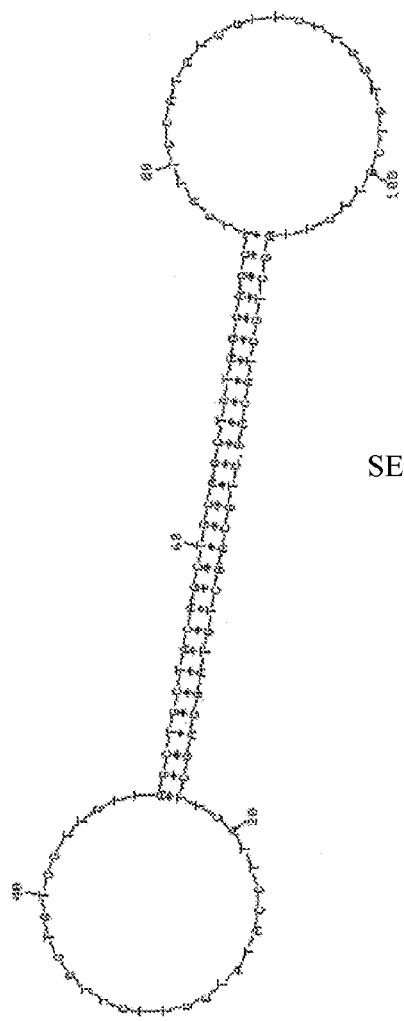

FIGS. 2 and 3 exemplify the two different secondary structures of the dSLIM molecules 30L1 (FIG. 2, SEQ ID NO: 28) (such as MS) and KG (FIG. 3, SEQ ID NO: 29) (such as ML, GS, GL, GLS) for the three loop sequences as calculated by "DNA mfold" (Conditions: 150 mM NaCl, 0.5 mM $MgCl_2$ and 37° C.). In contrast to 30L1, no base pairings in the loop were predicted for KG under the conditions selected.

Preparation of Various Monomeric and Multimeric Molecules

Figure 4:
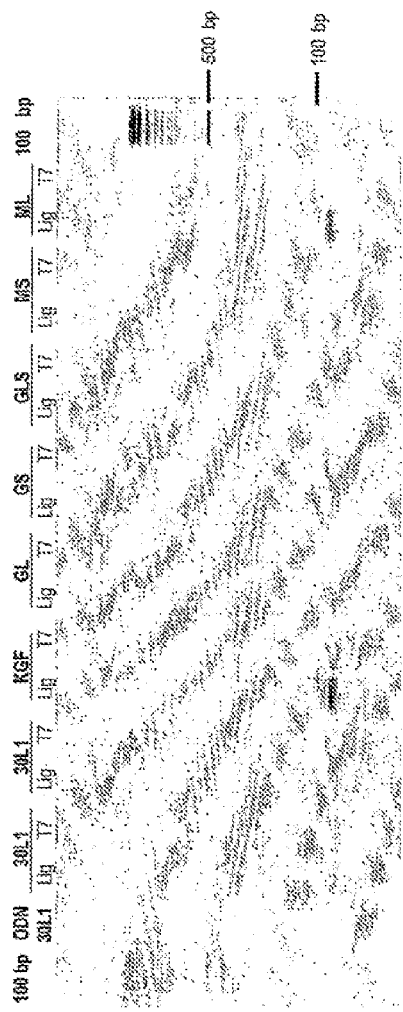
FIG. 4 shows the result of separation of 0.3 μg of ligation batches and test T7 digestion of the different dSLIM molecules along with the 30L1 ODN in 3% agarose gel (marker 100 bp 0.5 μg, ODN 30L1, each time ligation, T7 digestion: 30L1, 30L1, KGF, GL, GS, GLS, MS, ML).

FIG. 4 shows the result of separation of 0.3 µg of ligation batches and test T7 digestion of the different dSLIM molecules along with the 30L1 ODN in 3% agarose gel (marker 100 bp 0.5 µg, ODN 30L1, each time ligation, T7 digestion: 30L1, 30L1, KGF, GL, GS, GLS, MS, ML). In all lanes where the different molecules were separated, a band can be seen at a short distance below the level up to which the 100 bp fragment of the marker has migrated, which band corresponds to the monomeric molecule. In the lane containing the 30L1 ODN a band below the band of the monomeric molecules is visible. For molecules containing L3 (GL, GLS), a blurred distribution of DNA can be seen in the upper region of the gel up to the pockets, which is markedly stronger for GL and weaker for GLS in the T7 digestion batch compared to the ligation batch. For molecules containing long poly(G) motifs (GL, GS, GLS MS), the bands in the gel are relatively blurred compared to the other molecules (30L1, KG, ML). In the lanes where the T7 digestion batches were applied the fluorescence intensities, especially in the upper region of the gel, are lower compared to those lanes which had ligation batches applied thereon.

Figure 5A:
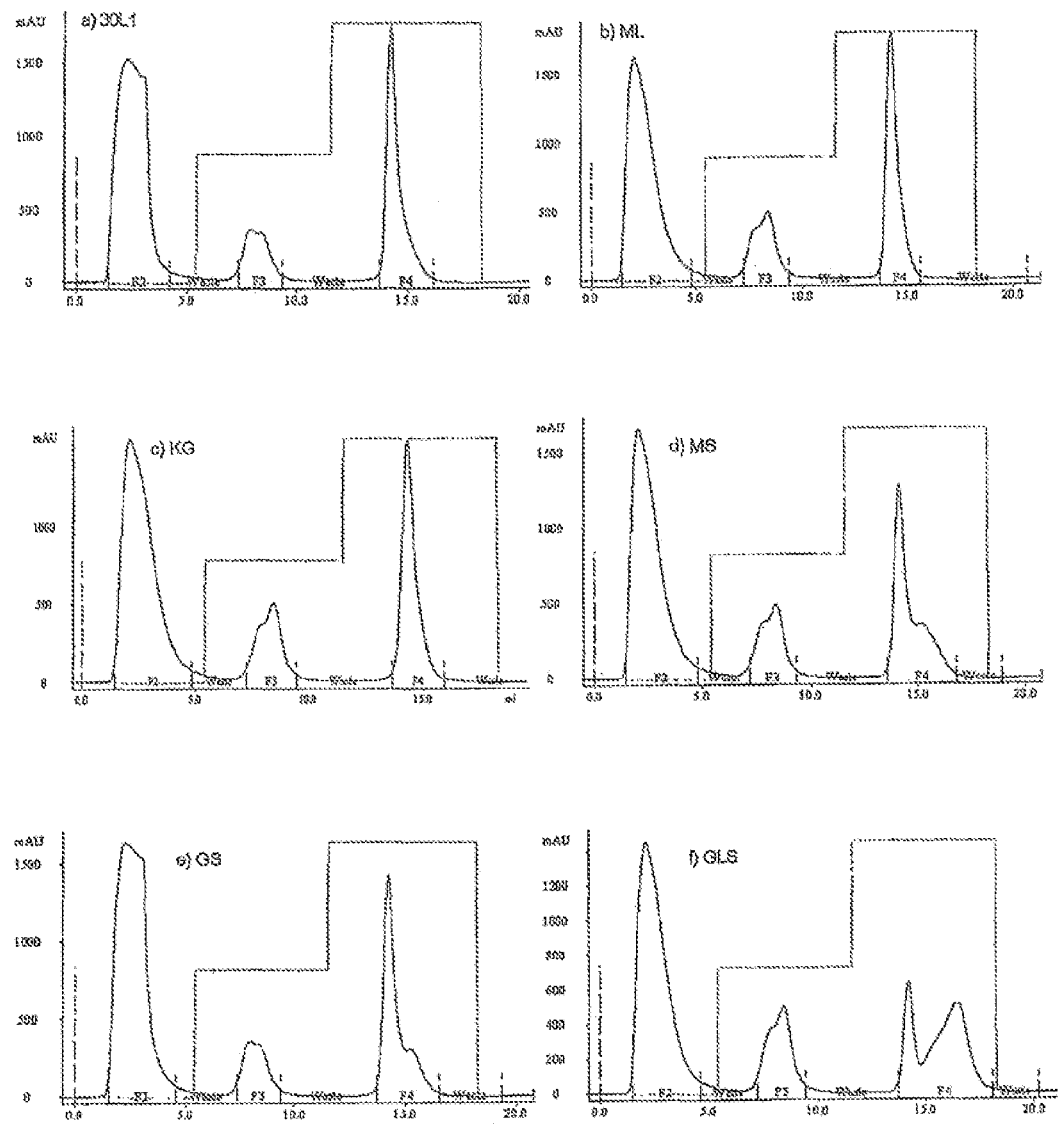
FIGS. 5A and 5B show the chromatograms of a subsequent HPLC purification of the different molecules.
Figure 5B:
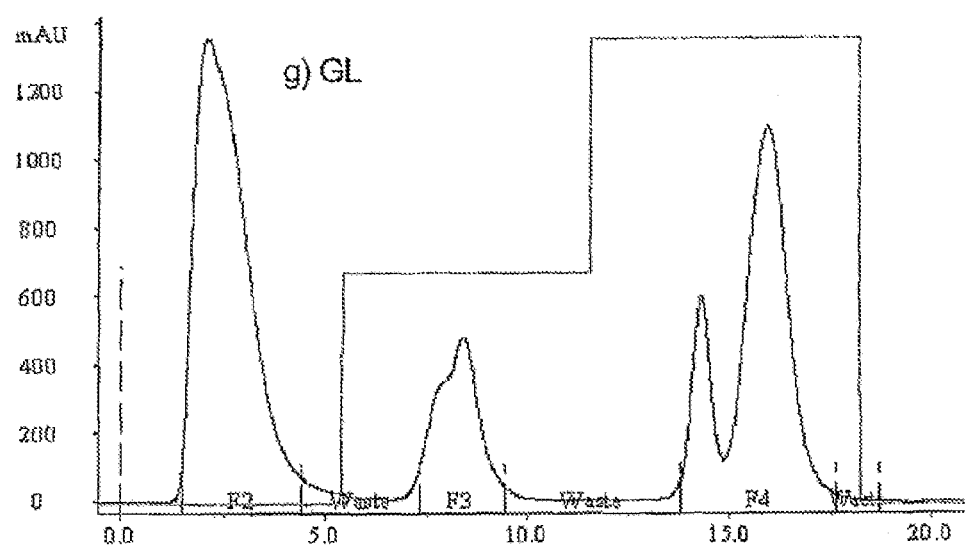

FIGS. 5A and 5B shows the chromatograms of a subsequent HPLC purification of the different molecules. Each one plots the absorption at 260 nm (blue line) versus the volume flowed through the column after injection of the sample to be separated (broken pink line). The green line represents the NaCl buffer gradient of 0%, 50% and 100% of the 1 M NaCl buffer (T20N1000). The first peak with its maximum at 2.5 ml and 0% T20N1000 (F2) corresponds to the unbound molecules, the second peak with its maximum at 8 ml and 50% T20N1000 (F3) corresponds to the molecules with low affinity to the stationary phase (despite applying the 12fold amount compared to the fraction F4, no DNA was detected in the agarose gel for either fractions).

The third peak with its maximum at 14 ml and 100% T20N1000 (F4) corresponds to the monomeric molecules.

FIGS. 5A and 5B: Chromatograms of HPLC purification of different monomeric and multimeric dSLIM molecules.

30L1, b) ML, c) KG, d) MS, e) GS, f) GLS, g) GL, column: 1 ml DMAE; amount applied: 700 µg; flow rate: 1 ml/min; buffer A: 20 mM Tris, pH 7; buffer B: 20 mM Tris, 1 M NaCl, pH7; gradient: 0%, 50%, 100% buffer B.

When comparing the chromatograms of the different molecules, it is clearly seen that F4 is a single peak for molecules containing no poly(G) motifs, i.e. neither S3 nor L3 (30L1, ML, KG). In contrast, a shoulder is observed at F4 for those molecules which contain S3. For molecules containing L3 (GL, GLS), the maximum has two peaks, with different intensity distribution between GL and GLS. For GLS, both partial maximums have about the same intensity, while for GL the partial maximum observed at higher volume has a higher intensity than that at lower volume. The appearing side maximums or shoulders were fractionated separately by manual operation. The fractions were designated F1 and F2 in accordance with the chronological order of their elution.

Figure 6:
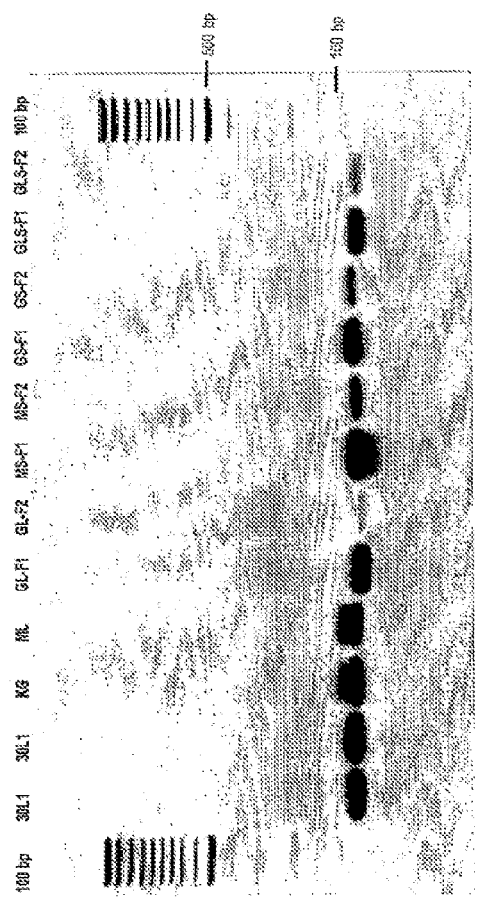
FIG. 6 shows application of a final product on the agarose gel.

The above-described dSLIM fractions of HPLC separation following ethanol precipitation, i.e. the final products, are applied on the agarose gel represented in FIG. 6. In all lanes the band corresponding to the monomeric molecules can be seen at a short distance below the migration distance of the 100 bp marker fragment. For ML and KG, a second, weaker band can be recognized a short distance above this band, which has a higher intensity for ML. GL, MS and GLS show a somewhat higher mobility in the gel than the other molecules. For molecules containing no long poly(G) motifs (30L1, KG, MS), a non-discrete intensity distribution up to the level of about 200 bp can be recognized above the dSLIM band. In addition, a weak band at the level of the 200 bp marker fragment can be recognized for KG and ML.

FIG. 6: Various monomeric and multimeric molecules after ethanol precipitation.

3% agarose gel, amount applied 0.3 µg, marker 100 bp 0.5 µg (100 bp, 30L1, 30L1, KG, ML, GL-F1, GL-F2, MS-F1, MS-F2, GS-F1, GS-F2 GLS-F1, GLS-F2, 100 bp).

For molecules where a multi-peak distribution was observed and the maximums were fractionated in HPLC purification, each fraction 1 mainly corresponds to the monomeric band, while the lanes which had the fractions 2 applied thereon mainly show an intensity distribution over a wide range above the monomeric band. Here, MS and GS have similar intensity distributions which, starting approximately from the monomeric band, extend up to a migration level corresponding to 500 bp. For GL, on the other hand, it starts above 200 bp, extending up to the pocket of the gel. For GLS, however, distribution of the DNA across the entire lane can be observed, starting from the monomeric band.

FIG. 7: Thermal denaturation of various monomeric and multimeric dSLIM molecules.

Native PAGE, 8% gel (2.6% C), amount applied 0.25 µg, marker 25 bp 0.3 µg (25 bp, untreated, denaturation 95° C. for 10 min: 30L1, MS, ML, KG, GS, GL-F2, GLS-F2).

The gel in FIG. 7 shows the effect of thermal denaturation of the different molecules on their migration behavior in the gel. To this end, the batches were divided and a part was heated to 95° C. for 10 minutes, immediately cooled on ice and applied. The bands observed correspond to those in the gel described under FIG. 7, but in this case, non-separated DNA is visible in the pocket of the gel for MS and GS as well, and a second band is seen for MS, which runs at the same level as the second band of 30L1. GS and MS involve a production batch different from the gel shown in FIG. 7, where the side maximums in HPLC fractionation were not collected separately. A comparison of the bands in gel with denatured and non-denatured dSLIM shows that the intensity of the $1^{st}$ band is decreased and that of the $2^{nd}$ band is increased in all molecules after heating. The band in the ML and KG lanes appearing in the upper third of the gel is no longer visible after denaturation. Also, the DNA in the pockets of the lanes where MS and GS were applied can no longer be recognized after denaturation. In the lanes GL-F2 and GLS-F2 the amount of DNA in the pocket is likewise reduced, but on the other hand a major number of regularly arranged bands is visible above the $2^{nd}$ band.

Figure 8:
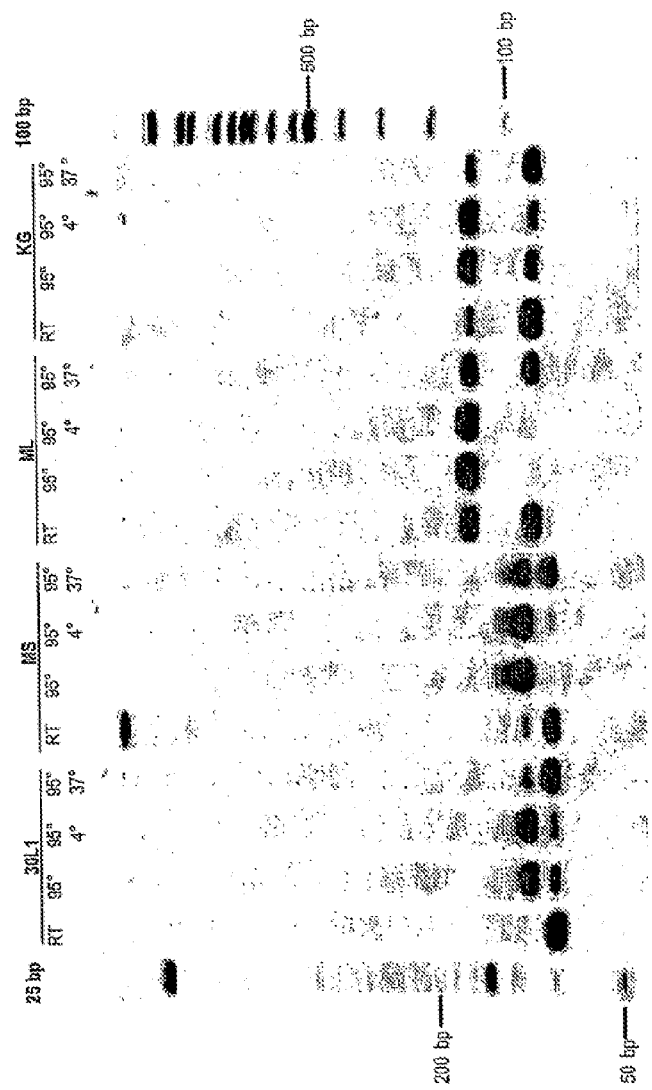
FIG. 8 shows thermal denaturation and renaturation of various dSLIM (native PAGE, 8% gel (2.6% C), amount applied 0.25 μg, marker 25 bp 0.3 μg, marker 100 bp 0.3 μg (25 bp, untreated, denaturation 95° C. 10 min, 3 d 4° C. after denaturation, 3 d 37° C. after denaturation: 30L1, MS, ML, KG, 100 bp)).
Figure 9:
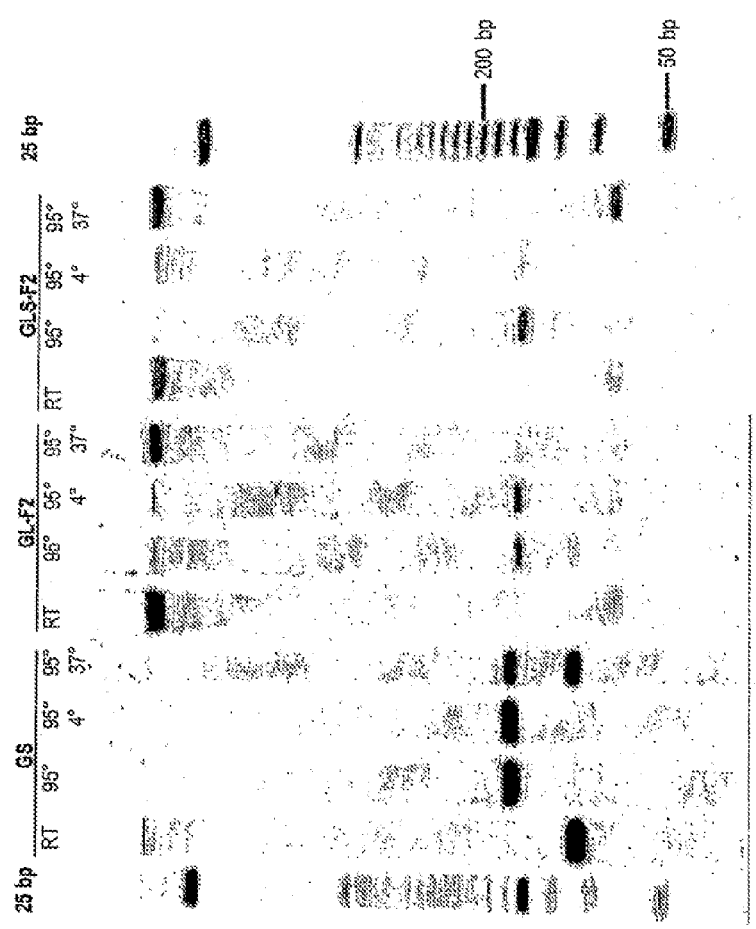
FIG. 9 shows thermal denaturation and renaturation of various dSLIM (native PAGE, 8% gel (2.6% C), amount applied 0.25 μg, marker 25 bp 0.3 μg, marker 100 bp 0.3 μg (25 bp, untreated, denaturation 95° C. 10 min, 3 d 4° C. after denaturation, 3 d 37° C. after denaturation: GS, GL-F2, GLS-F2, 100 bp)).

To examine whether the changes caused by denaturation are reversible, the denatured samples were divided and incubated for 3 days at 4° C. and 37° C., respectively. The untreated dSLIM batches were stored at 4° C., likewise divided after 3 days, and one aliquot each time was heated to 95° C. for 10 minutes and immediately placed on ice. The results of a native PAGE used to separate the batches are represented in FIGS. 8 and 9. FIG. 8 shows thermal denaturation and renaturation of various dSLIM (native PAGE, 8% gel (2.6% C), amount applied 0.25 µg, marker 25 bp 0.3 µg, marker 100 bp 0.3 µg (25 bp, untreated, denaturation 95° C. 10 min, 3 d 4° C. after denaturation, 3 d 37° C. after denaturation: 30L1, MS, ML, KG, 100 bp)). FIG. 9 shows thermal denaturation and renaturation of various dSLIM (native PAGE, 8% gel (2.6% C), amount applied 0.25 µg, marker 25 bp 0.3 µg, marker 100 bp 0.3 µg (25 bp, untreated, denaturation 95° C. 10 min, 3 d 4° C. after denaturation, 3 d 37° C. after denaturation: GS, GL-F2, GLS-F2, 100 bp)). The untreated and denatured samples show the same migration behavior in the gel as described for the gel represented in FIG. 7. In their migration behavior, the denatured samples incubated at 4° C. correspond to the samples denatured immediately prior to application. The samples incubated at 37° C. show a migration behavior in the gel, which largely corresponds to that of the untreated samples. However, the intensity of the second band for 30L1, MS and GS is higher than for the above. Another difference for GS and MS is seen in the amount of DNA having remained in the pocket of the gel, which is very low compared to the untreated sample.

Dimeric Molecule and Monomeric 30L1 Fractions

To examine whether the band recognized in the upper third is a band corresponding to a dimer, a fraction (F3) obtained from a large amount of monomeric molecules by means of HPLC separation and representing this band was applied on a native PAGE together with the dimer molecule 60L1.

Figure 10:
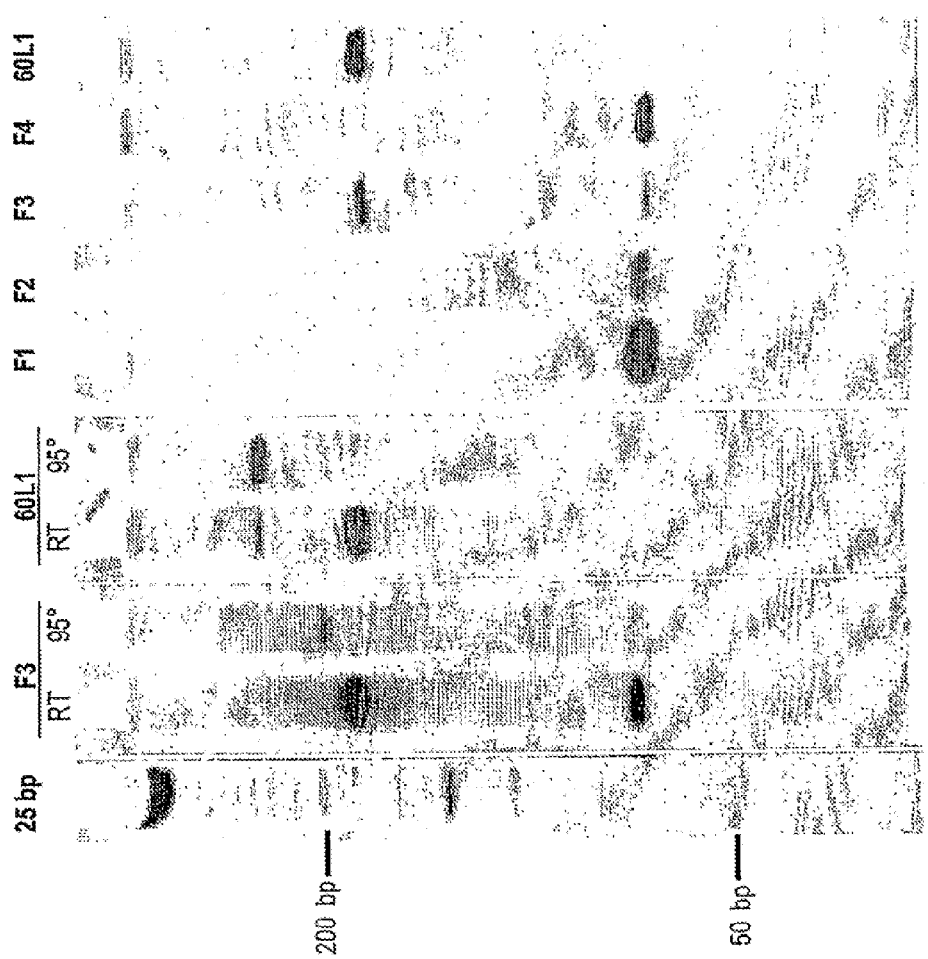
FIG. 10 shows a comparison of fraction 3 with dimer molecule 60L1.

FIG. 10: Comparison of fraction 3 with dimer molecule 60L1.

Native PAGE, 8% gel (5% C), amount applied 0.25 µg, marker 25 bp 0.3 µg (25 bp, F3, F3 95° C., 60L1, 60L1 95° C., fraction 1 (F1), fraction 2 (F2), fraction 3 (F3), fraction 4 (F4) from HPLC purification of dSLIM 30L1, 60L1).

The bands observed run at the same level. When applying samples in denatured form on a gel, the bands are found at a higher level in the gel compared to a lane having untreated samples applied thereon. The corresponding lanes of the native PAGE are represented in FIG. 10 together with the result of separation of the four different fractions of monomer 30L1 obtained by means of HPLC fractionation.

Incubation Medium, Protein Binding

To investigate the effect of the conditions in the cell culture, especially the presence of proteins, on the molecules used for stimulation, the latter were incubated in cell culture medium for 0.5 and 27 h at 37° C. and separated along with the molecules dissolved in water using native PAGE. Following DNA staining, the proteins present in the medium were detected in the gel by means of Coomassie staining. The results are represented in FIGS. 11 and 12.

Figure 11:
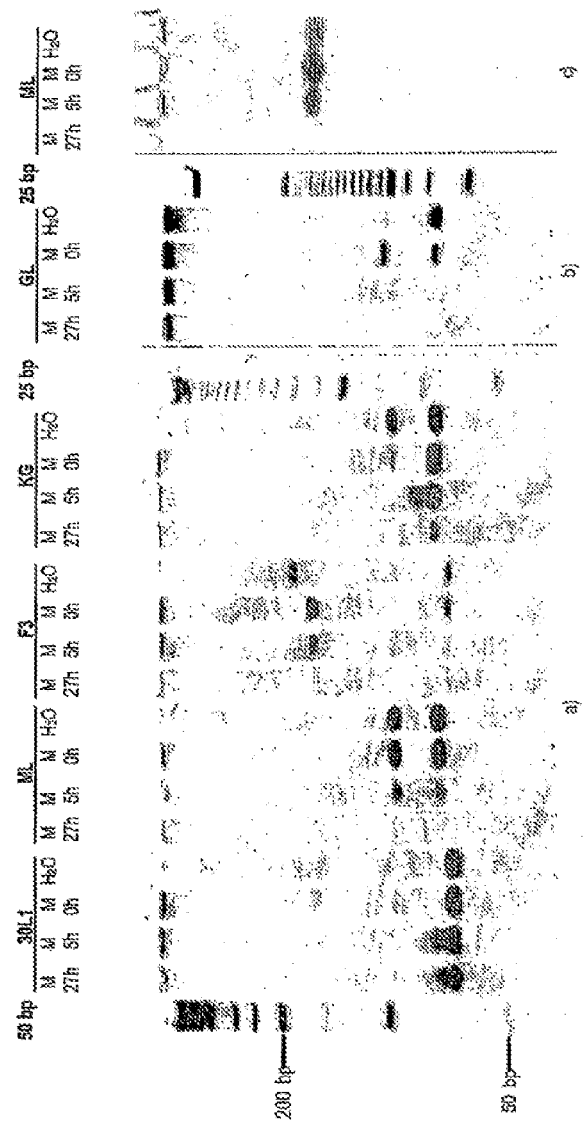
FIG. 11 shows the ethidium bromide-stained PAGE having the molecules applied thereon ((a) and (b) and gives an exemplary representation (c) of a section from the Coomassie-stained gel used to compare the migration distances.
Figure 12:
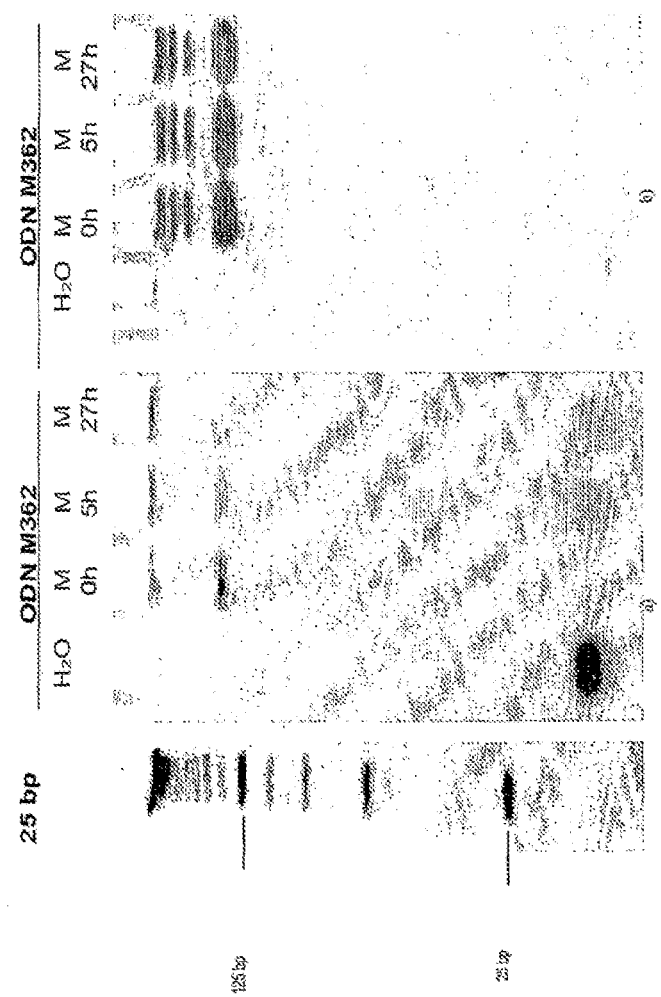
FIG. 12 shows the native PAGE wherein the phosphorothioate-protected control molecule M362 was applied.

FIG. 11: Incubation of monomeric molecules (dSLIM) in medium a) Native PAGE, 8% gel (5% C), amount applied 0.25 µg, marker 25 bp 0.3 µg, marker 50 bp 0.3 µg (50 bp, 27 h medium, 5 h medium, 0 h medium, $H_2O$: 30L1, ML, F3, KG, 25 bp).

b) Native PAGE, 8% gel (2.6% C), amount applied 0.25 µg, 25 bp 0.35 µg (27 h medium, 5 h medium, 0 h medium, $H_2O$: GL, 25 bp).

c) Section of Coomassie staining, native 8% PAGE (5% C), of FIG. 12 a) (27 h medium, 5 h medium, 0 h medium, $H_2O$: ML).

FIGS. 11 a) and 11 b) show the ethidium bromide-stained PAGE having the molecules applied thereon. FIG. 11 c) gives an exemplary representation of a section from the Coomassie-stained gel used to compare the migration distances. Comparison of the lanes including the different batches shows that a band appears in the gel pocket for all molecules in medium, which is absent in the $H_2O$ lanes (with the exception of GL). The band appearing in the upper region of the gel in $H_2O$ for 30L1 and fraction 3 shows a shorter migration distance in medium which is at the level of the lower protein band. The intensity of both DNA and protein bands decreases with increasing incubation time. For GL, the intensity of the $2^{nd}$ band increases in medium compared to $H_2O$.

Figure 13:
FIG. 13 shows incubation of dSLIM and ODN M362 in medium with and without FCS. a) Native PAGE, 4-20% gel, amount M362 applied 0.05 μg, marker 25 bp 0.2 μg (25 bp, H$_2$O, medium without FCS (M−), medium with FCS (M+), 24 h medium with FCS); b) Section of Coomassie staining, native PAGE, 4-20% gel, of a) (25 bp, H$_2$O, medium without FCS (M−), medium with FCS (M+), 24 h medium with FCS); c) Native PAGE, 4-20% gel, amount KG applied 0.12 μg, marker 25 bp 0.2 μg (25 bp, H$_2$O, medium without FCS (M−), medium with FCS (M+), 24 h medium with FCS); d) Section of Coomassie staining, native PAGE, 4-20% gel, of c) (25 bp, H$_2$O, medium without FCS (M−), medium with FCS (M+), 24 h medium with FCS).

FIG. 12: Incubation of ODN M362 in medium a) Native PAGE, 12% gel (5% C), amount applied 0.25 µg, marker 25 bp 0.3 µg (25 bp, $H_2O$, 0 h medium, 5 h medium, 27 h medium).

b) Section from Coomassie staining, native PAGE, 12% gel (5% C), of FIG. 13 a) ($H_2O$, 0 h medium, 5 h medium, 27 h medium).

FIG. 12 shows the native PAGE wherein the phosphorothioate-protected control molecule M362 was applied. As clearly seen therein, the DNA band visible in $H_2O$ at the bottom edge of the gel has disappeared in medium. Instead, a band at the upper edge of the gel, corresponding in its migration distance to the lower protein band (FIG. 12 b), and a band in the gel pocket can be seen. A decrease in the intensity of the DNA bands with increasing incubation time can be observed in this case as well.

To verify that the changes observed were caused by the presence of proteins rather than other components of the medium, the molecules were also diluted in medium without addition of FCS for comparison. In FIG. 13 the corresponding lanes of the gels are exemplified for dSLIM (KG) and M362. FIG. 13 shows incubation of dSLIM and ODN M362 in medium with and without FCS. a) Native PAGE, 4-20% gel, amount M362 applied 0.05 µg marker 25 bp 0.2 µg (25 bp, $H_2O$, medium without FCS (M−), medium with FCS (M+), 24 h medium with FCS); b) Section of Coomassie staining, native PAGE, 4-20% gel, of a) (25 bp, $H_2O$, medium without FCS (M−), medium with FCS (M+), 24 h medium with FCS); c) Native PAGE, 4-20% gel, amount KG applied 0.12 µg, marker 25 bp 0.2 µg (25 bp, $H_2O$, medium without FCS (M−), medium with FCS (M+), 24 h medium with FCS); d) Section of Coomassie staining, native PAGE, 4-20% gel, of c) (25 bp, $H_2O$, medium without FCS (M−), medium with FCS (M+), 24 h medium with FCS). The lanes where the ODNs and the molecules were separated in medium with no FCS correspond in their intensity distribution to those where the ODNs and dSLIMs were applied as a solution in water. In contrast, the ODNs dissolved in medium with FCS and the molecules show a migration behavior in the native PAGE which corresponds to that described in FIGS. 11 and 12 for those lanes where monomeric molecules and ODNs diluted in medium were applied.

Immunostimulatory Effect: Stimulation of PBMC

The immunomodulatory effect of the different molecules was investigated on PBMC isolated from human blood donations. To this end, the PBMC were incubated with the respective molecule or control molecule M362 at a final concentration of 1 µM for 48 h, and the amount of IL-6, IFN-α and IFN-γ in the cell culture supernatants was measured using ELISA. Cells incubated with no additives were used as control.

The ELISA results of PBMC supernatants isolated from 4 blood donations (donors A-D) are represented in the diagrams in FIG. 14). The respective values correspond to the mean values of double determinations, and the error bars represent the double standard deviation determined therefrom. For values marked with *, additional double determinations for stimulation of PBMC were performed, and the values indicated correspond to the mean values of the four ELISA results obtained. The error bars correspond to the double standard deviation of these four values.

FIG. 14 a-c): Results ELISA IFN-γ (a), IFN-α (b), IL-6 (c) PBMC

Supernatants PBMC ($2.4 \times 10^6$ cells per batch in 600 µl) from different donors A-D, stimulation 48 h with 1 µM dSLIM/ODN M362, standard measuring range - - - , * double determination cell culture, error bars: 2× standard deviation from double determination ELISA (* double determination cell culture+double determination ELISA=4 values).

Referring to the diagrams, an immediately striking feature is that the cytokine concentrations in the supernatants of the different donors show strong variations, thereby impeding comparison of the data. The standard deviations of the values additionally determined in the cell culture as double determinations are comparable to the standard deviations merely determined from the double determinations in the ELISA, indicating that the differences are due to differences in the PBMC. In the unstimulated batches, no or only very low cytokine concentrations were detected for all donors. In the determination of the IL-6 and IFN-γ concentrations some of the values determined are at the upper limit or outside the standard measuring range which is up to 10,000 µg/ml for IFN-γ, up to 3,500 µg/ml for IL-6 for dSLIM and 7,000 µg/ml for M362.

To allow better comparison of data from the different donors, the resulting cytokine values were normalized. To this end, the percentage of the determined cytokine concentrations in the value determined for M362 was calculated for each donor. The mean values of the thus-normalized data from the four donors are represented in the diagrams in FIG. 15 a-c). Each error bar corresponds to the mean value deviation. Due to the great differences observed between the individual donors, the error bars are very large. At least, however, it is possible to estimate a tendency for the individual molecules by means of the diagrams.

Figure 15A:
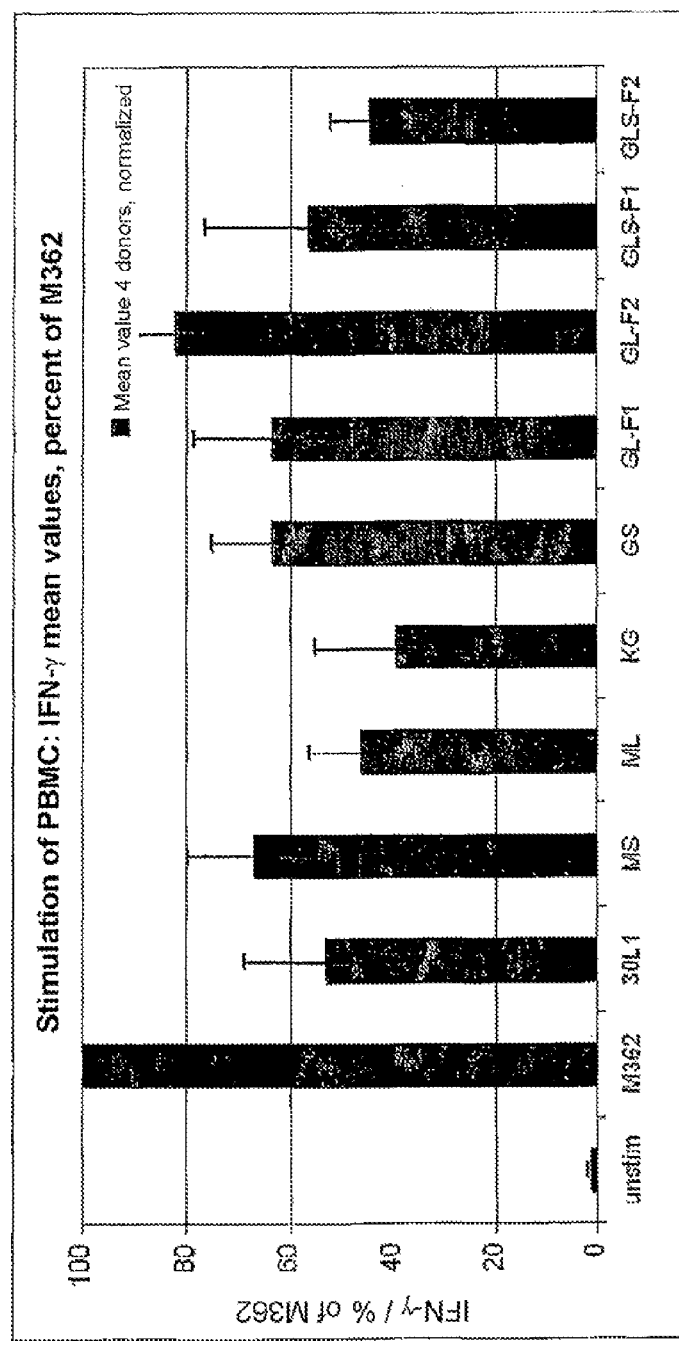
FIGS. 15A, 15B and 15C show diagrams of the mean values of the thus-normalized data from the four donors.
Figure 15B:
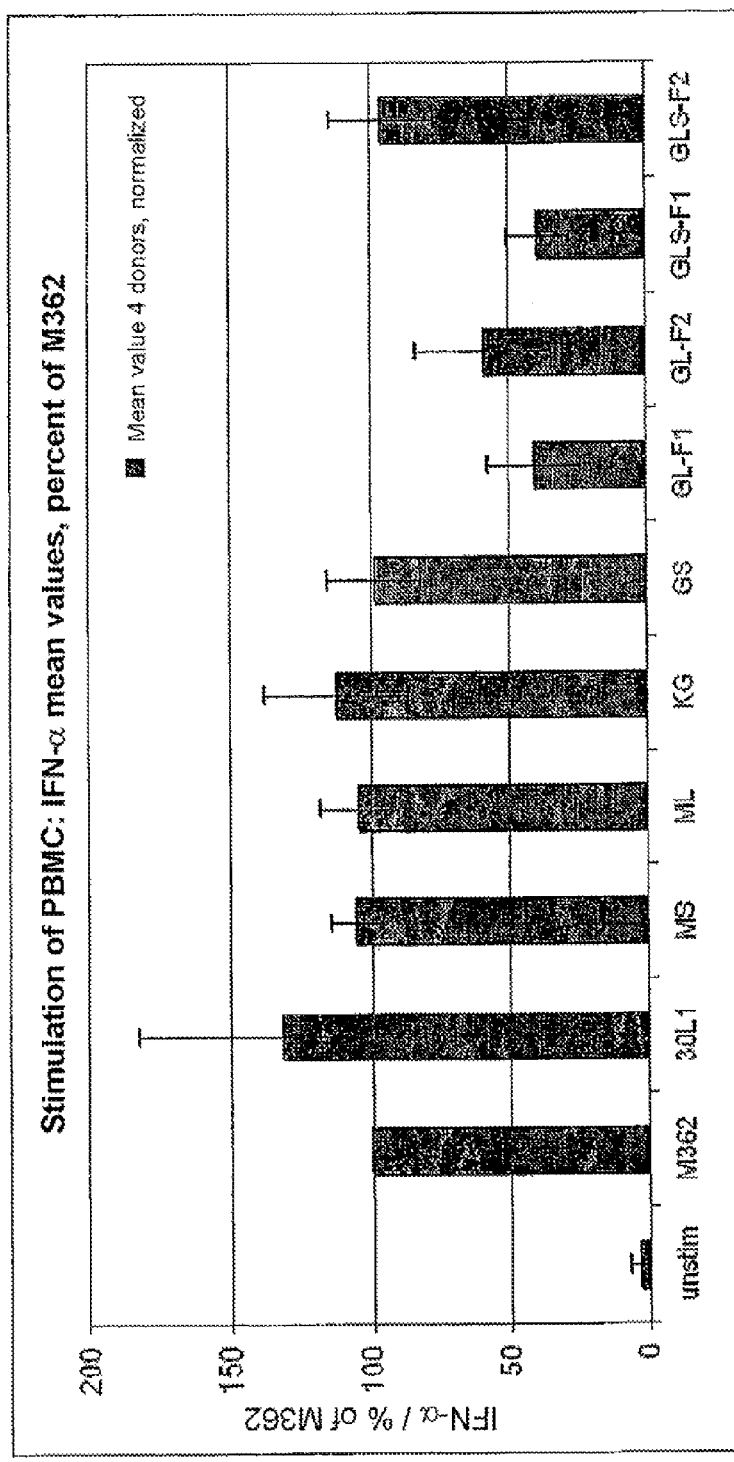
Figure 15C:
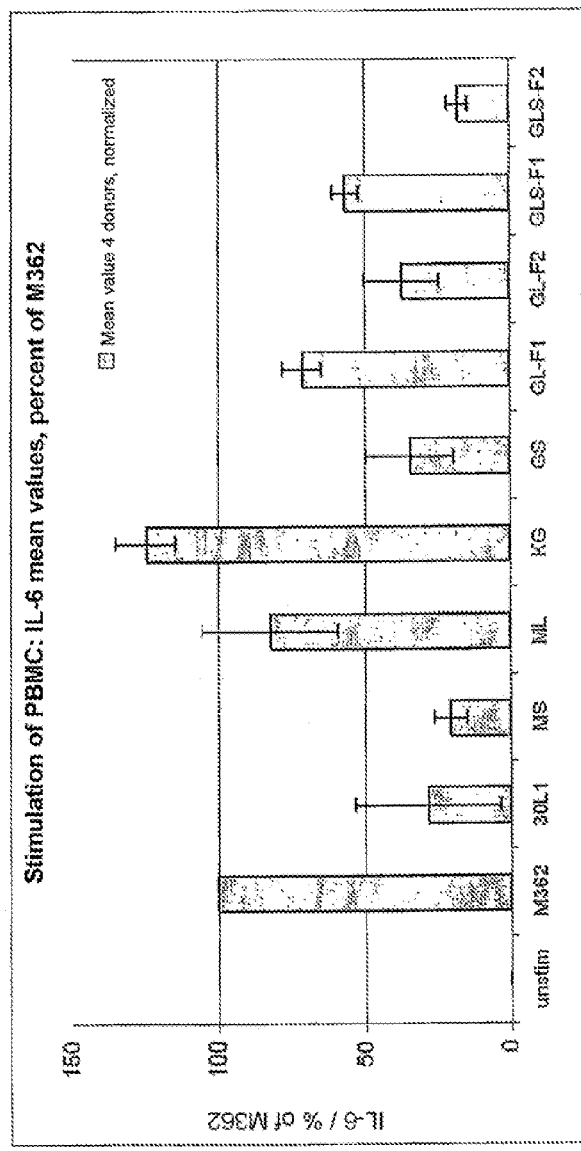

FIG. 15 a-c): Normalized mean values of ELISA results for IFN-γ (a), IFN-α (b), IL-6 (c).

Figure 14A:
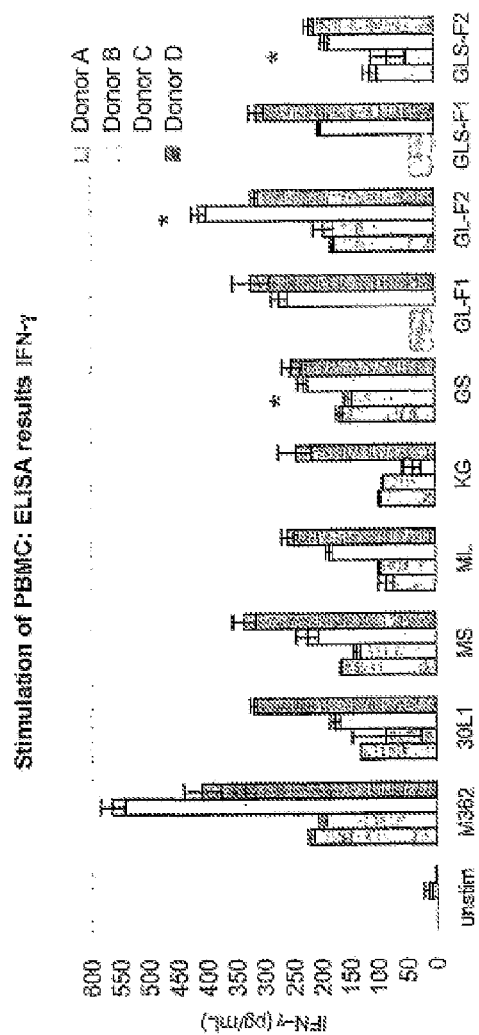
FIGS. 14A, 14B and 14C show diagrams of the ELISA results of PBMC supernatants isolated from 4 blood donations (donors A-D).
Figure 14B:
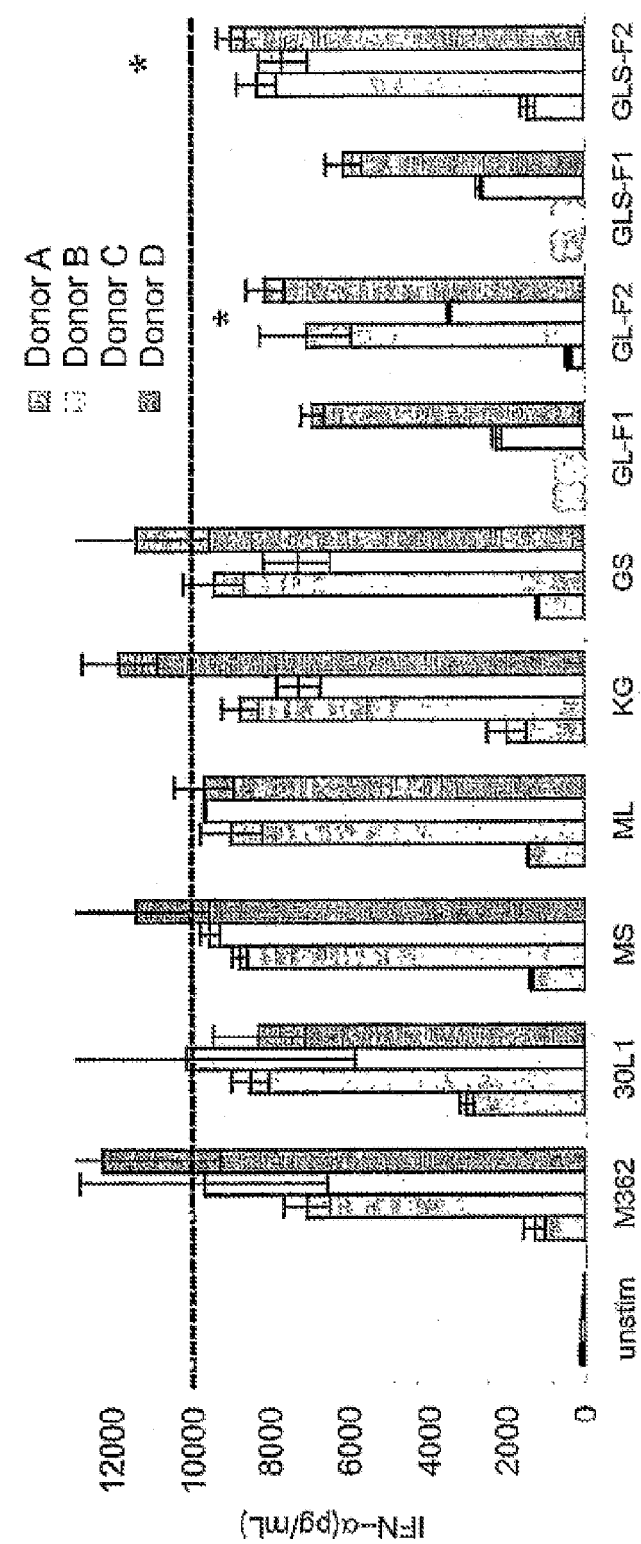
Figure 14C:
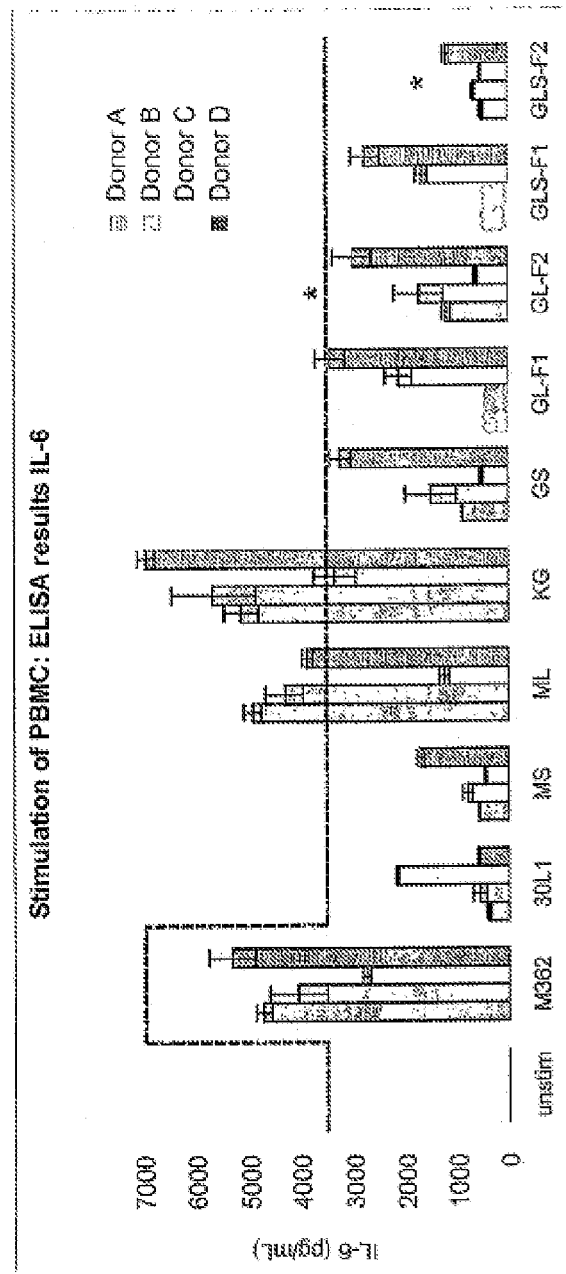

Results of ELISA see FIGS. 14A, 14B and 14C normalized: amount cytokine in % M362 per donor, mean values of 4 donors, error bars: mean value deviation.

For IFN-γ, the calculated values for the tested molecules were between 40% and 80%, relative to the values of M362, and the values for KG, ML, and GLS-F2 were rather in the lower and for GL-F2 in the upper region.

The percent mean values of the different constructs for IFN-α roughly corresponded to those of M362, with the exception of the values calculated for GL-F1, GLS-F1 and GL-F2 which were only about 50% of the M362 values.

The mean values of the percentages M362 for IL-6 were below 50% for 30L1, MS, GS, GL-F2 and GLS-F2, and MS and GLS-F2—the constructs with the lowest endotoxin concentration—also had the lowest values. The values for GL-F1 and GL-F2, where no endotoxin values are available, were slightly above 50%, relative to M362. The highest IL-6 values, which correspond to those of M362 or are above 100%, were found in cells stimulated with KG and ML. Also, the highest endotoxin concentration was measured for the two constructs.

Figure 16A:
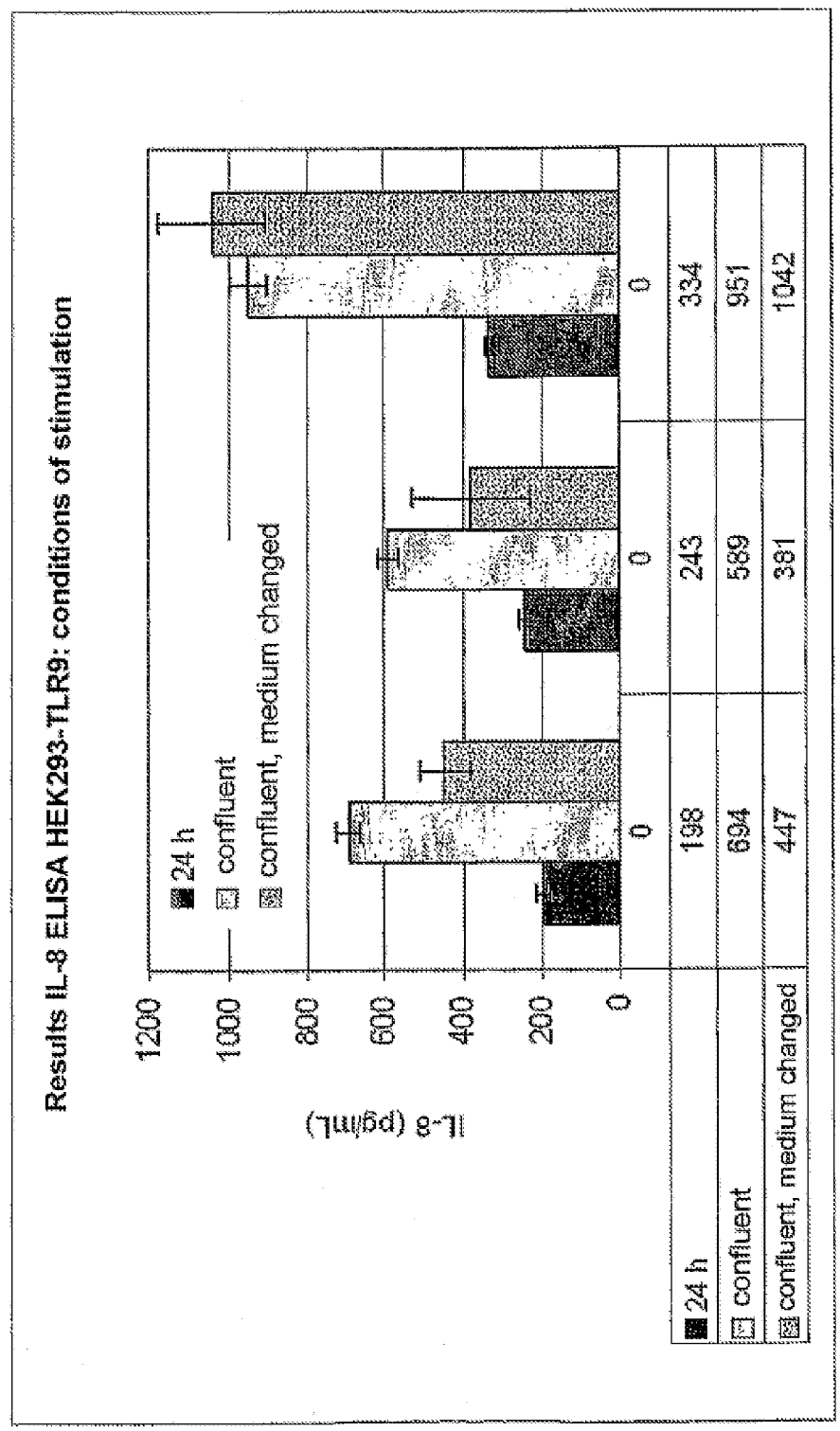
FIGS. 16A and 16B show the results of ELISA IL-8 HEK293-TLR9, conditions of stimulation.
Figure 16B:
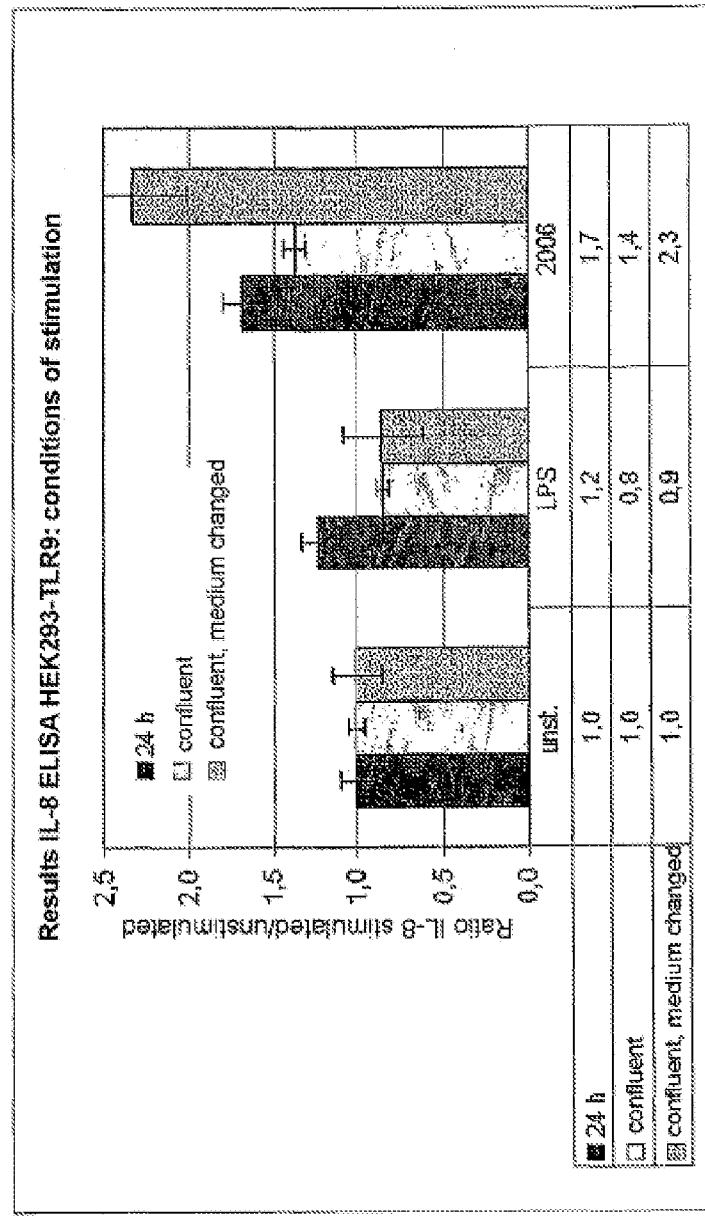

FIGS. 16A and 16B show the results of ELISA IL-8 HEK293-TLR9, conditions of stimulation.

Figure 17A:
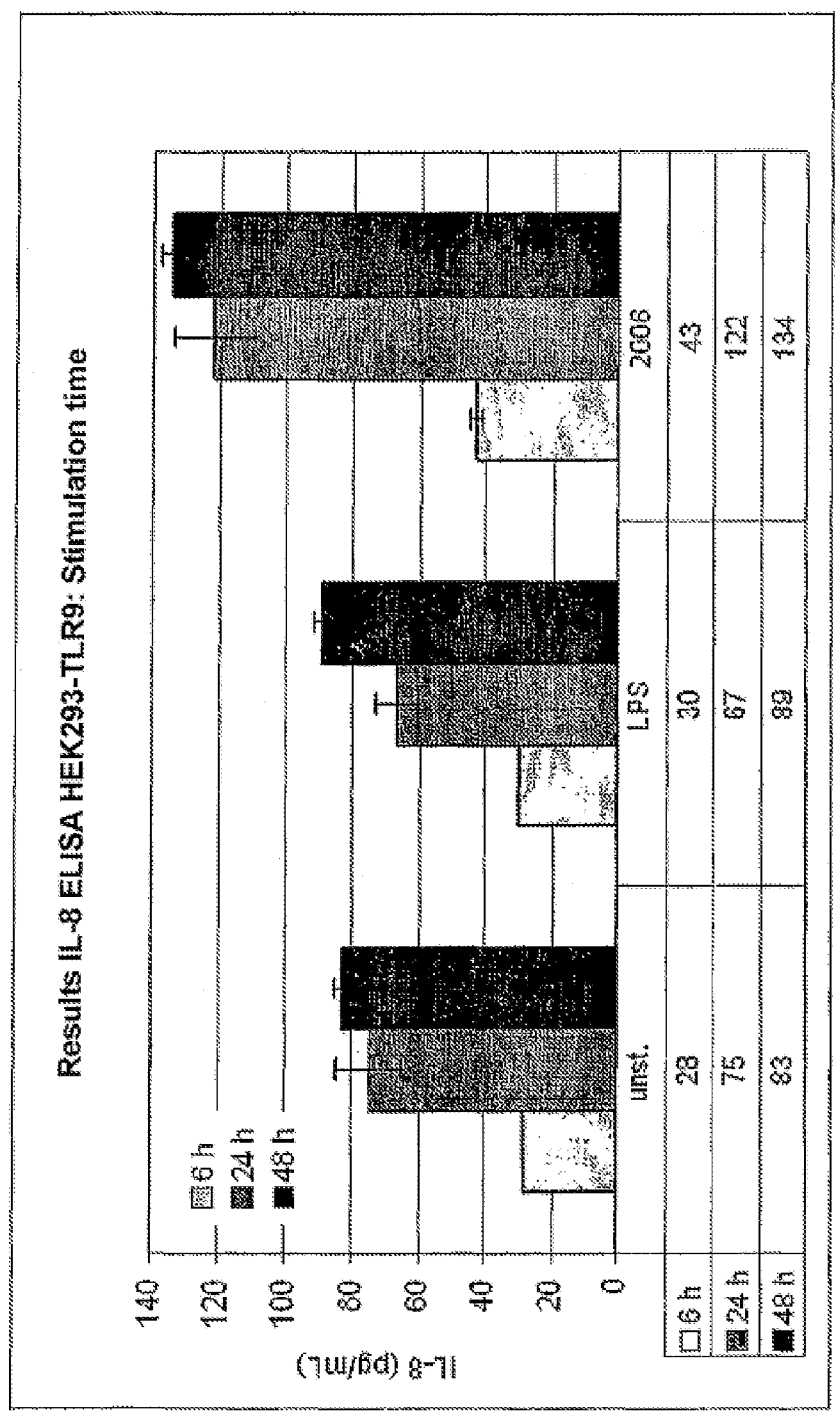
FIGS. 17A and 17B show results of ELISA IL-8 HEK293-TLR9 stimulation time.
Figure 17B:
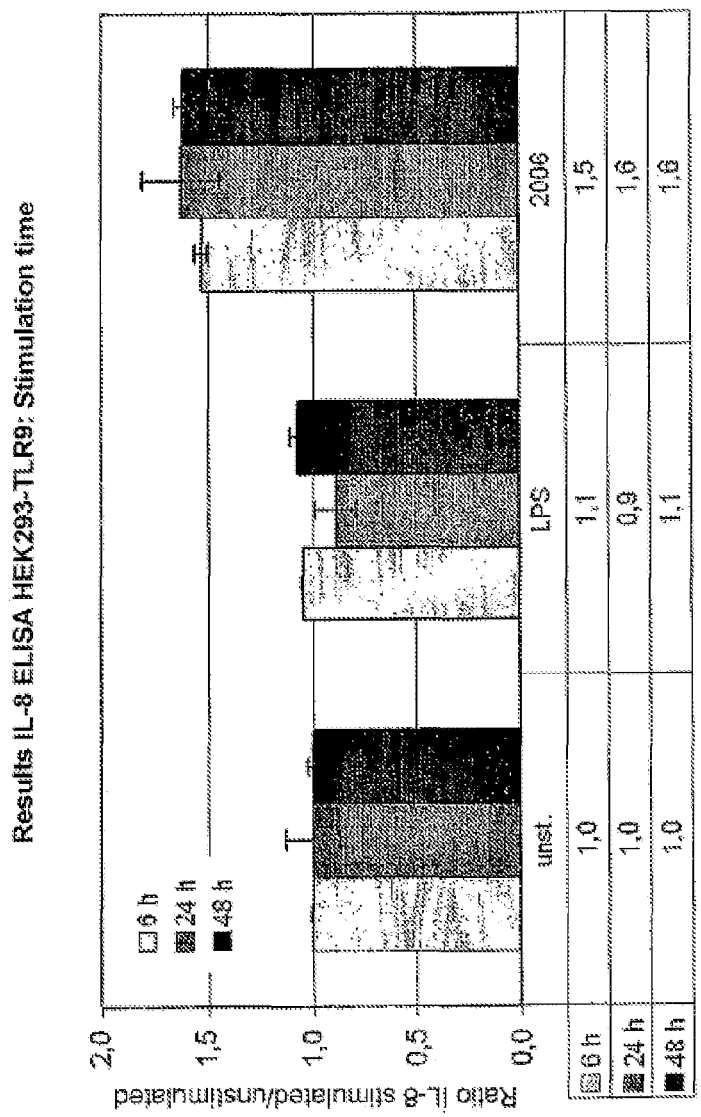
Figure 18A:
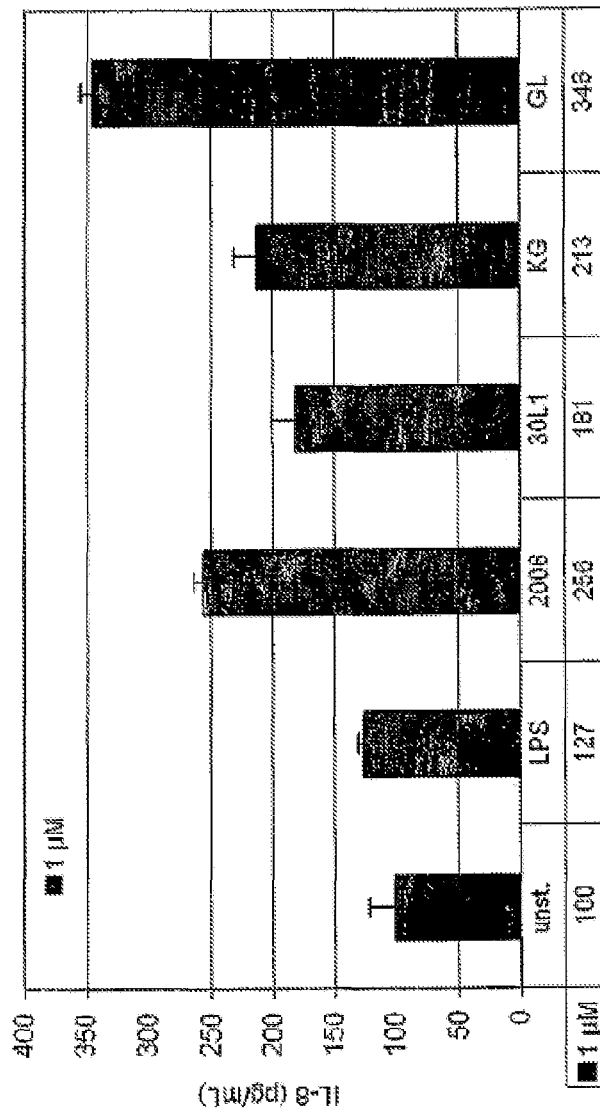
FIGS. 18A, 18B, 18C and 18D show the results of ELISA IL-8 HEK293-TLR9, various dSLIMs.
Figure 18B:
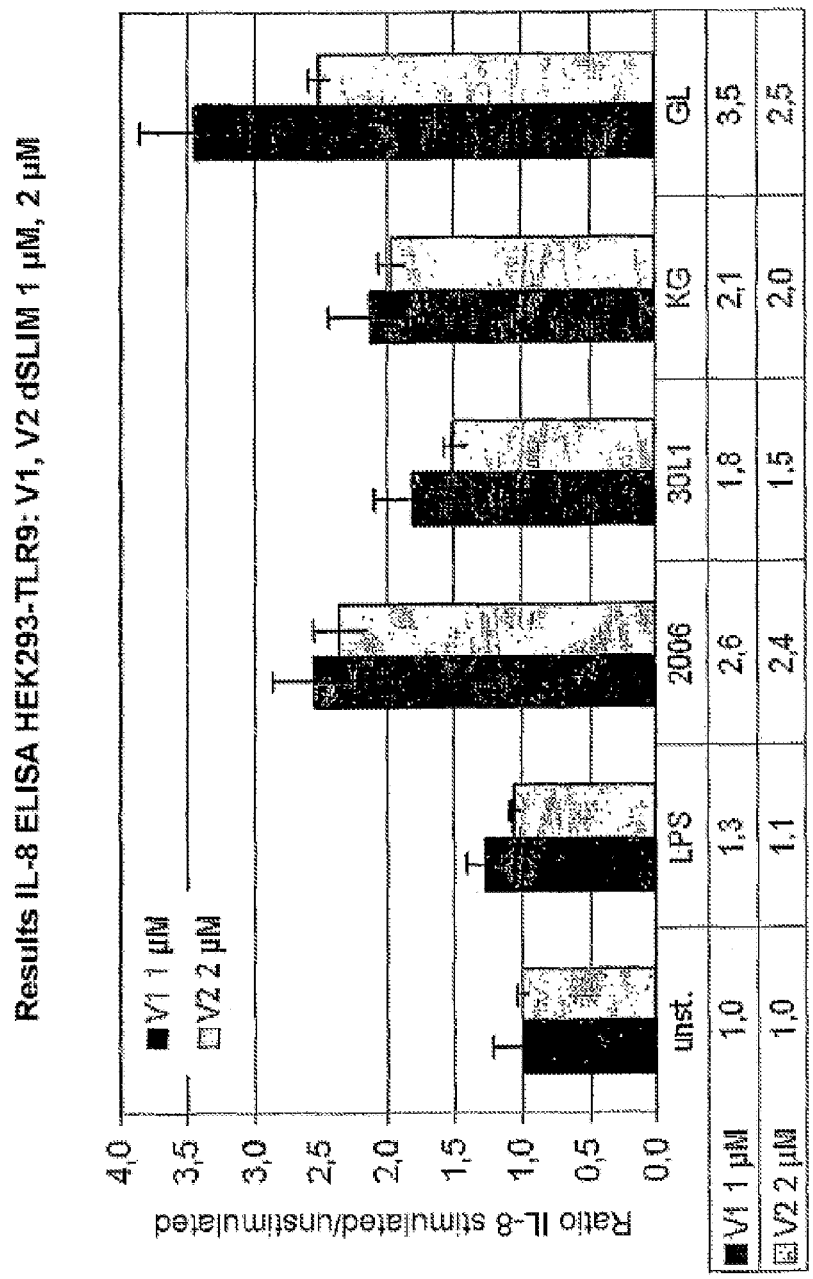
Figure 18C:
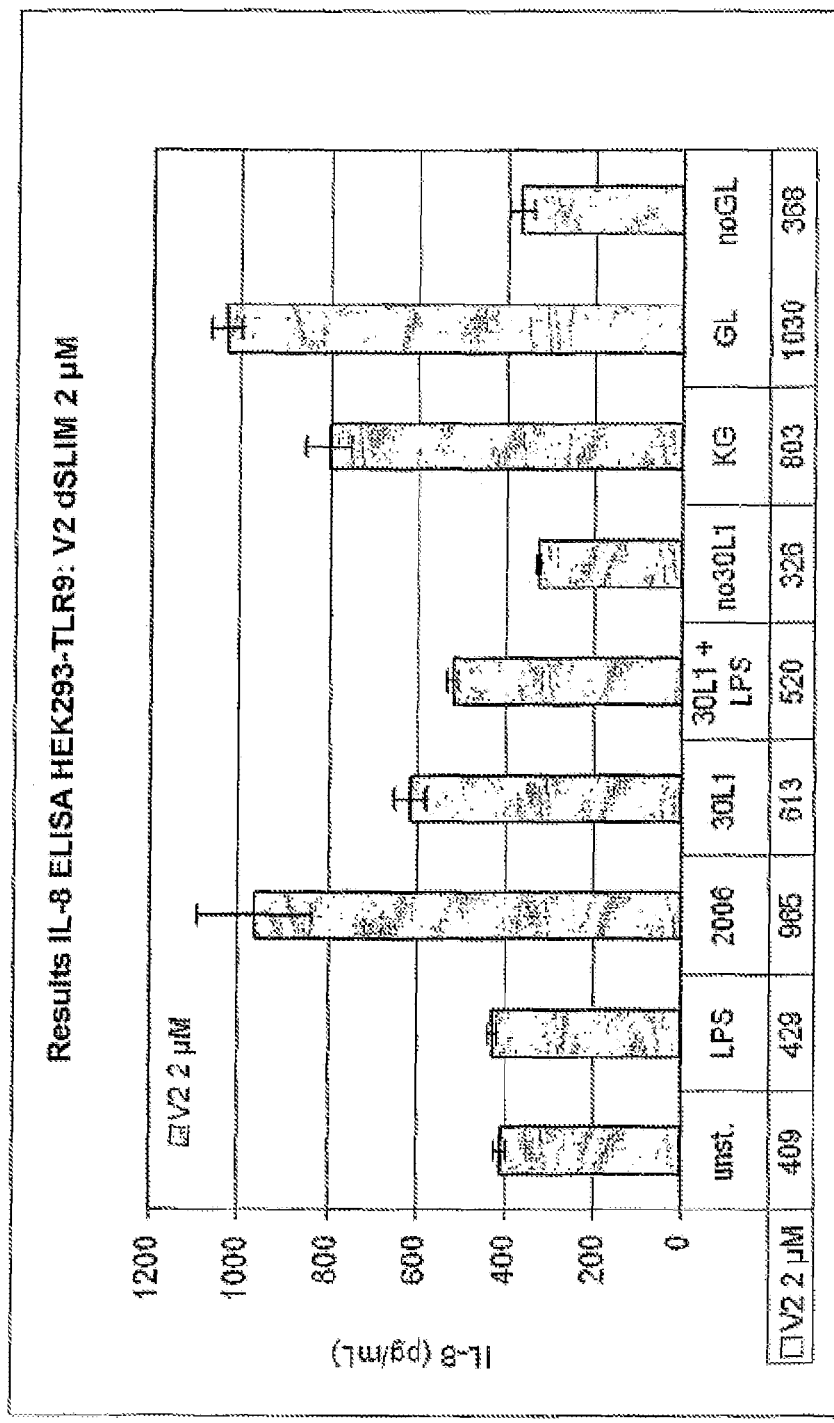
Figure 18D:
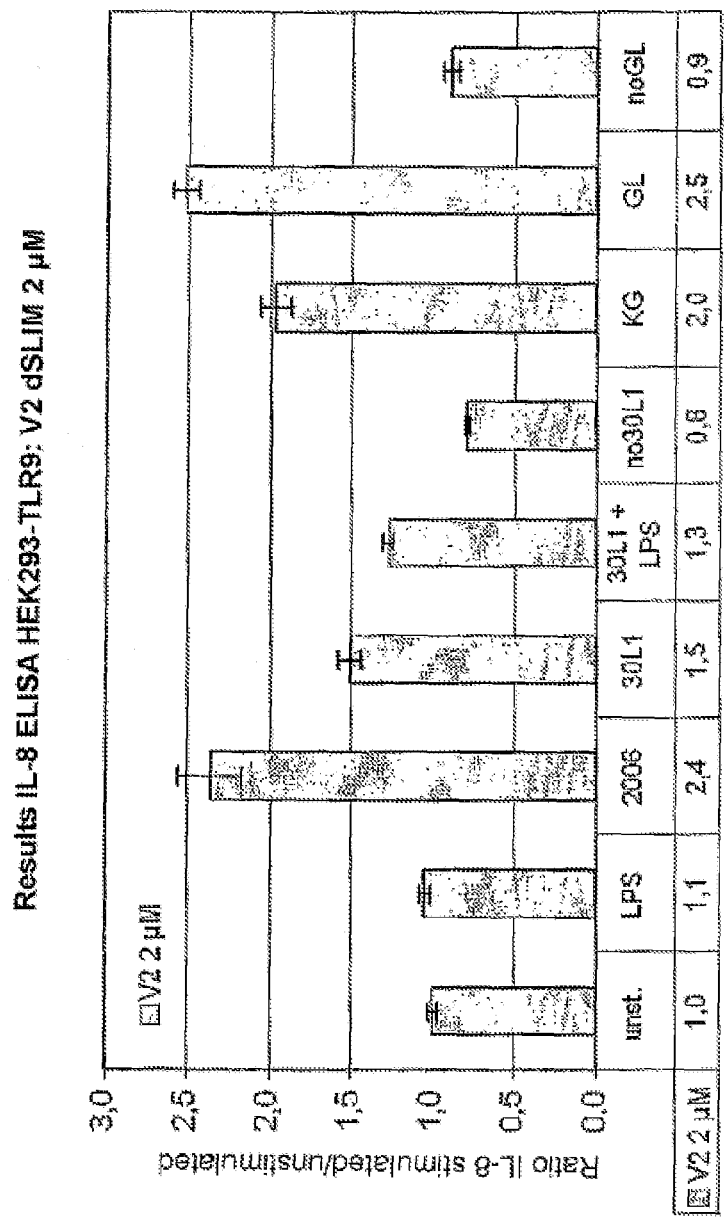

FIGS. 17A and 17B: Results of ELISA IL-8 HEK293-TLR9 stimulation time

Supernatants HEK293-TLR9: 400 µl/batch ($5 \times 10^6$ cells/ml); stimulation 6 h, 24 h, 48 h with 2.5 µM of ODN 2006; 0.5 µg/ml LPS; stimulation 3 days after cell seeding (medium changed after 48 h and prior to stimulation); error bars: 2× standard deviation from ELISA double determination.

Ratios of amounts chemokine in stimulated/unstimulated batches from a); error bars: sum of relative errors from ELISA double determination.

The chemokine concentrations measured are relatively low. However, an increase of the IL-8/CXCL8 amount with increasing incubation time can be observed in all batches, which, however, becomes very low from 24 h to 48 h. Here as well, the respective values for LPS-stimulated and unstimulated cells are approximately equal in magnitude, and those for cells stimulated with ODN 2006 are increased by a factor of 1.5 compared to unstimulated cells. No difference can be recognized in the ratios of IL-8/CXCL8 amounts of stimulated/unstimulated batches determined at different points in time, for which reason further stimulations were effected for 24 h.

FIGS. 18A-D show the results of ELISA IL-8 HEK293-TLR9, various dSLIMs.

Figure 19A:
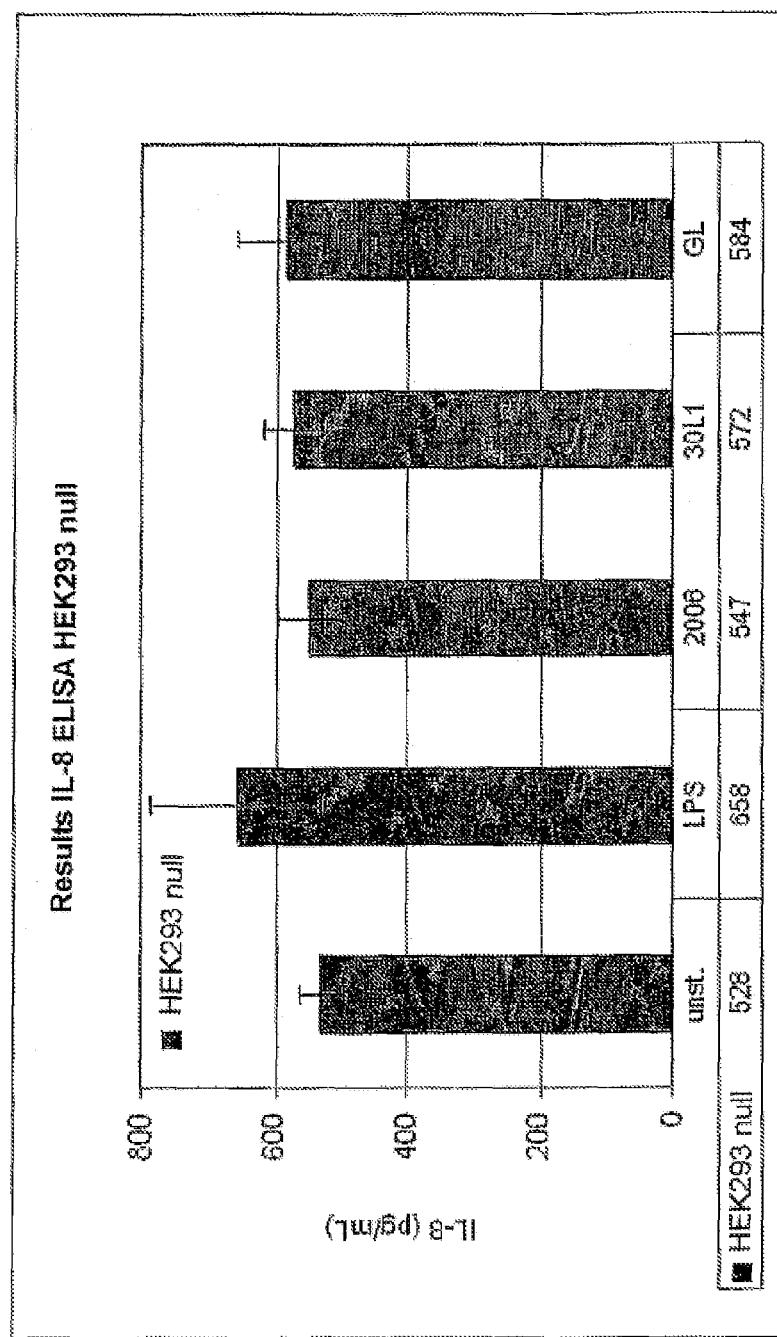
FIGS. 19A and 19B show results of ELISA IL-8 HEK293 null of various monomeric molecules (dSLIM).
Figure 19B:
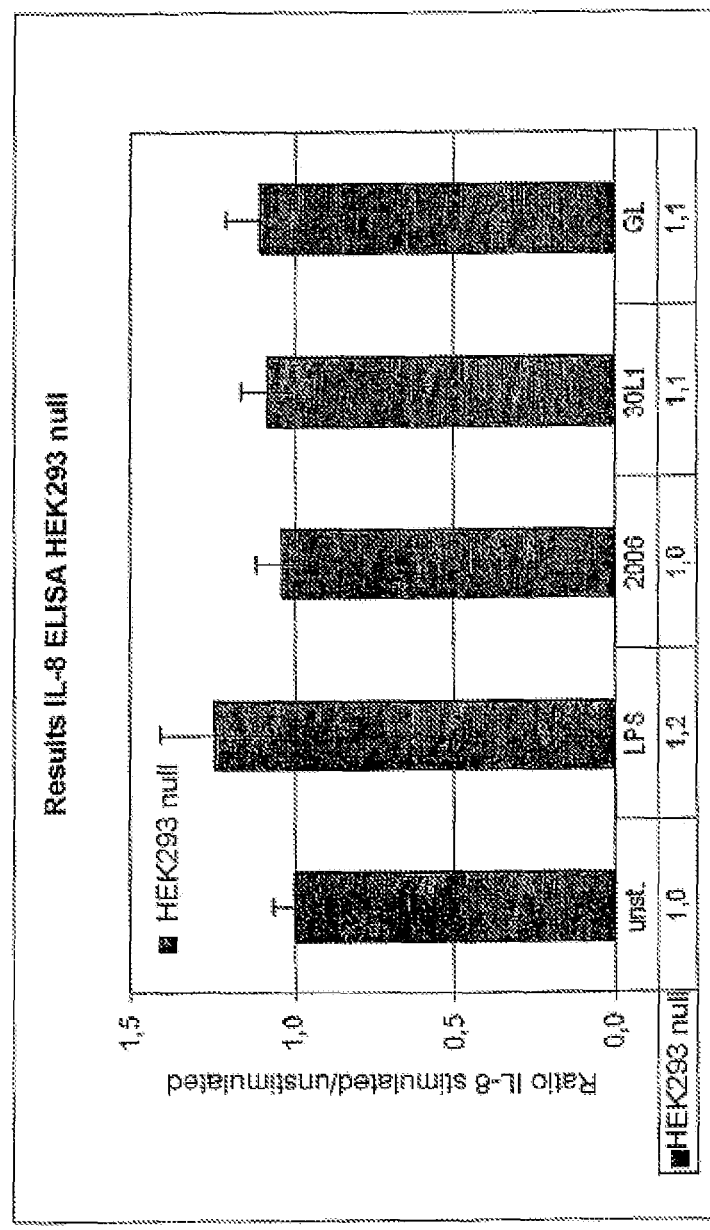

FIGS. 19A and B: Results ELISA IL-8 HEK293 null of various monomeric molecules (dSLIM).

a) Supernatants HEK293 null: 400 µl/batch ($1 \times 10^6$ cells/ml); stimulation for 24 h with 2 µM ODN 2006/dSLIM; 0.5 µg/ml LPS; stimulation 4 days after cell seeding (medium changed after 48 h and prior to stimulation); error bars: 2× standard deviation from ELISA double determination.

b) Ratios of amounts chemokine in stimulated/unstimulated batches from a); error bars: sum of relative errors from ELISA double determination.

No significant difference in IL-8/CXCL8 secretion compared to an unstimulated batch is observed in any of the batches incubated with said different stimulants.

The invention claimed is:

1. A multimeric molecule for modulating the activity of the human or animal immune system, comprising:
   at least two covalently closed stem-loop monomer structures,
   at least one G structures,
   wherein the molecule comprises the base sequence $N^1N^2CGN^3N^4$ wherein $N^1N^2$ is an element from the group of GT, GG, GA, AT or AA, $N^3N^4$ is an element from the group of CT or TT, and C is deoxycytosine, G is deoxyguanosine, A is deoxyadenosine, and T is deoxythymidine.

2. The molecule according to claim 1, comprising the following sequences:
   a) GTTCCTGGAG ACGTTCTTAG GAACGTTCTC CTTGACGTTG GAGAGAAC (SEQ ID NO: 1), or
   b) ACCTTCCTTG TACTAACGTT GCCTCAAGGA AGGTTGATCT TCATAACGTT GCCTAGATCA (SEQ ID NO: 2), or
   c) an oligodeoxyribonucleic acid sequence having the base sequence AACG TTCTTCGGGG CGTT (SEQ ID NO: 3),
   wherein said sequence has a length of 40 to 1,600 nucleotides.

3. The molecule according to claim 1, wherein the base sequence according to feature c) is included in the sequence CCTAGGGGTT ACCACCTTCA TTGGAAAACG TTCTTCGGGG CGTTCTTAGG TGGTAACC CCTAGGGGTT ACCACCTTCA TTGGAAAACG TTCTTCGGGG CGTTCTTAGG TGGTAACC (SEQ ID NO: 4).

4. The molecule according to claim 1, comprising a partially single-stranded, covalently closed chain of deoxyribonucleoside residues.

5. The molecule according to claim 1, wherein the base sequence $N^1N^2CGN^3N^4$ is situated in the single-stranded region of the closed chain of deoxyribonucleoside residues.

6. The molecule according to claim 1, wherein one or more substituents are linked to the molecule via covalent bonds.

7. The molecule according to claim 6, wherein the substituent is selected from the group consisting of peptides, proteins, saccharides, antigenic structures, DNA and/or RNA.

8. A kit comprising the molecule according to claim 1 and optionally information relating to combining the contents of the kit.

9. A pharmaceutical agent comprising a molecule according to claim 1, optionally together with a pharmaceutically tolerable carrier.

* * * * *

SEQUENCE LISTING

```
<160> NUMBER OF SEQ ID NOS: 29

<210> SEQ ID NO 1
<211> LENGTH: 48
<212> TYPE: DNA
<213> ORGANISM: Artificial Sequence
<220> FEATURE:
<223> OTHER INFORMATION: Synthesized, Circular single-stranded with stem
      loop structure (dumbbell), all phosphodiester

<400> SEQUENCE: 1
gttcctggag acgttcttag gaacgttctc cttgacgttg gagagaac                48

<210> SEQ ID NO 2
<211> LENGTH: 60
<212> TYPE: DNA
<213> ORGANISM: Artificial Sequence
<220> FEATURE:
<223> OTHER INFORMATION: Synthesized, Circular single-stranded with stem
      loop structure (dumbbell), all phosphodiester

<400> SEQUENCE: 2
accttccttg tactaacgtt gcctcaagga aggttgatct tcataacgtt gcctagatca    60

<210> SEQ ID NO 3
<211> LENGTH: 18
<212> TYPE: DNA
<213> ORGANISM: Artificial Sequence
<220> FEATURE:
<223> OTHER INFORMATION: Synthesized, Circular single-stranded with stem
      loop structure (dumbbell), all phosphodiester

<400> SEQUENCE: 3
aacgttcttc ggggcgtt                                                  18

<210> SEQ ID NO 4
```

-continued

<211> LENGTH: 116
<212> TYPE: DNA
<213> ORGANISM: Artificial Sequence
<220> FEATURE:
<223> OTHER INFORMATION: Synthesized, Circular single-stranded with stem
      loop structure (dumbbell), all phosphodiester

<400> SEQUENCE: 4
cctaggggtt accaccttca ttggaaaacg ttcttcgggg cgttcttagg tggtaacccc     60
taggggttac caccttcatt ggaaaacgtt cttcggggcg ttcttaggtg gtaacc        116

<210> SEQ ID NO 5
<211> LENGTH: 58
<212> TYPE: DNA
<213> ORGANISM: Artificial Sequence
<220> FEATURE:
<223> OTHER INFORMATION: Synthesized oligodeoxynucleotide, 30L1, all
      phosphodiester

<400> SEQUENCE: 5
cctaggggtt accaccttca ttggaaaacg ttcttcgggg cgttcttagg tggtaacc      58

<210> SEQ ID NO 6
<211> LENGTH: 58
<212> TYPE: DNA
<213> ORGANISM: Artificial Sequence
<220> FEATURE:
<223> OTHER INFORMATION: Synthesized oligodeoxynucleotide, KG, all
      phosphodiester

<400> SEQUENCE: 6
ctgcagctgt agcagcttca ttccatatcg ttcttcgtgt cgttcttagc tgctacag      58

<210> SEQ ID NO 7
<211> LENGTH: 58
<212> TYPE: DNA
<213> ORGANISM: Artificial Sequence
<220> FEATURE:
<223> OTHER INFORMATION: Synthesized oligodeoxynucleotide, ML, all
      phosphodiester

<400> SEQUENCE: 7
cctaggggtt accaccttca ttccatatcg ttcttcgtgt cgttcttagg tggtaacc      58

<210> SEQ ID NO 8
<211> LENGTH: 58
<212> TYPE: DNA
<213> ORGANISM: Artificial Sequence
<220> FEATURE:
<223> OTHER INFORMATION: Synthesized oligodeoxynucleotide, MS, all
      phosphodiester

<400> SEQUENCE: 8
cctaggggtg ggggccttca ttggaaaacg ttcttcgggg cgttcttagg cccccacc      58

<210> SEQ ID NO 9
<211> LENGTH: 58
<212> TYPE: DNA
<213> ORGANISM: Artificial Sequence
<220> FEATURE:
<223> OTHER INFORMATION: Synthesized oligodeoxynucleotide, GL, all
      phosphodiester

<400> SEQUENCE: 9
ctgcagctgt agcagcttcg gggggtatcg ttcttcgtgt cgttcttagc tgctacag      58

```
<210> SEQ ID NO 10
<211> LENGTH: 58
<212> TYPE: DNA
<213> ORGANISM: Artificial Sequence
<220> FEATURE:
<223> OTHER INFORMATION: Synthesized oligodeoxynucleotide, GS, all
      phosphodiester

<400> SEQUENCE: 10
cctaggggtg ggggccttca ttccatatcg ttcttcgtgt cgttcttagg cccccacc        58

<210> SEQ ID NO 11
<211> LENGTH: 58
<212> TYPE: DNA
<213> ORGANISM: Artificial Sequence
<220> FEATURE:
<223> OTHER INFORMATION: Synthesized oligodeoxynucleotide, GLS, all
      phosphodiester

<400> SEQUENCE: 11
cctaggggtg ggggccttcg gggggtatcg ttcttcgtgt cgttcttagg cccccacc        58

<210> SEQ ID NO 12
<211> LENGTH: 58
<212> TYPE: DNA
<213> ORGANISM: Artificial Sequence
<220> FEATURE:
<223> OTHER INFORMATION: Synthesized oligodeoxynucleotide, no30L1, all
      phosphodiester

<400> SEQUENCE: 12
cctaggggtt accaccttca ttggaaaatg ttctttgggg tgttcttagg tggtaacc        58

<210> SEQ ID NO 13
<211> LENGTH: 59
<212> TYPE: DNA
<213> ORGANISM: Artificial Sequence
<220> FEATURE:
<223> OTHER INFORMATION: Synthesized oligodeoxynucleotide, noGL, all
      phosphodiester

<400> SEQUENCE: 13
ctgcagctgt agcagctttg gggggtattg ttctttcgtg ttgttcttag ctgctacag       59

<210> SEQ ID NO 14
<211> LENGTH: 62
<212> TYPE: DNA
<213> ORGANISM: Artificial Sequence
<220> FEATURE:
<223> OTHER INFORMATION: Synthesized oligodeoxynucleotide, 60L1 forw,
      all phosphodiester

<400> SEQUENCE: 14
cctaggggtt accaccttca ttggaaaacg ttcttcgggg cgttctttcc ccaatggtgg      60
aa                                                                    62

<210> SEQ ID NO 15
<211> LENGTH: 62
<212> TYPE: DNA
<213> ORGANISM: Artificial Sequence
<220> FEATURE:
<223> OTHER INFORMATION: Synthesized oligodeoxynucleotide, 60L1 rev, all
      phosphodiester

<400> SEQUENCE: 15 cccctteeac cattggggat cattggaaaa cgttcttcgg ggcgttctta ggtggtaacc     60
``` cc                                                                          62

<210> SEQ ID NO 16
<211> LENGTH: 52
<212> TYPE: DNA
<213> ORGANISM: Artificial Sequence
<220> FEATURE:
<223> OTHER INFORMATION: Synthesized oligodeoxynucleotide, 30L1-AGGG,
      all phosphodiester

<400> SEQUENCE: 16
ggggttacca ccttcattgg aaaacgttct tcgggggctt cttaggtggt aa          52

<210> SEQ ID NO 17
<211> LENGTH: 25
<212> TYPE: DNA
<213> ORGANISM: Artificial Sequence
<220> FEATURE:
<223> OTHER INFORMATION: Synthesized oligodeoxynucleotide, M362, all
      phosphorothioate

<400> SEQUENCE: 17
tcgtcgtcgt tcgaacgacg ttgat                                       25

<210> SEQ ID NO 18
<211> LENGTH: 24
<212> TYPE: DNA
<213> ORGANISM: Artificial Sequence
<220> FEATURE:
<223> OTHER INFORMATION: Synthesized oligodeoxynucleotide, 2006, all
      phosphorothioate

<400> SEQUENCE: 18
tcgtcgtttt gtcgttttgt cgtt                                        24

<210> SEQ ID NO 19
<211> LENGTH: 30
<212> TYPE: DNA
<213> ORGANISM: Artificial Sequence
<220> FEATURE:
<223> OTHER INFORMATION: Synthesized oligodeoxynucleotide, L1, all
      phosphodiester

<400> SEQUENCE: 19
tcattggaaa acgttcttcg ggcgttctt                                   30

<210> SEQ ID NO 20
<211> LENGTH: 30
<212> TYPE: DNA
<213> ORGANISM: Artificial Sequence
<220> FEATURE:
<223> OTHER INFORMATION: Synthesized oligodeoxynucleotide, L2, all
      phosphodiester

<400> SEQUENCE: 20
tcattccata tcgttcttcg tgtcgttctt                                  30

<210> SEQ ID NO 21
<211> LENGTH: 30
<212> TYPE: DNA
<213> ORGANISM: Artificial Sequence
<220> FEATURE:
<223> OTHER INFORMATION: Synthesized oligodeoxynucleotide, L3, all
      phosphodiester

<400> SEQUENCE: 21 tcgggggta tcgttcttcg tgtcgttctt                                   30

<210> SEQ ID NO 22
<211> LENGTH: 17
<212> TYPE: DNA
<213> ORGANISM: Artificial Sequence
<220> FEATURE:
<223> OTHER INFORMATION: Synthesized oligodeoxynucleotide, S1 5' end,
      all phosphodiester

<400> SEQUENCE: 22
cctaggggtt accacct                                                   17

<210> SEQ ID NO 23
<211> LENGTH: 11
<212> TYPE: DNA
<213> ORGANISM: Artificial Sequence
<220> FEATURE:
<223> OTHER INFORMATION: Synthesized oligodeoxynucleotide, S1 3' end,
      all phosphodiester

<400> SEQUENCE: 23
aggtggtaac c                                                         11

<210> SEQ ID NO 24
<211> LENGTH: 17
<212> TYPE: DNA
<213> ORGANISM: Artificial Sequence
<220> FEATURE:
<223> OTHER INFORMATION: Synthesized oligodeoxynucleotide, S2 5' end,
      all phosphodiester

<400> SEQUENCE: 24
ctgcagctgt agcagct                                                   17

<210> SEQ ID NO 25
<211> LENGTH: 11
<212> TYPE: DNA
<213> ORGANISM: Artificial Sequence
<220> FEATURE:
<223> OTHER INFORMATION: Synthesized oligodeoxynucleotide, S2 3' end,
      all phosphodiester

<400> SEQUENCE: 25
agctgctaca g                                                         11

<210> SEQ ID NO 26
<211> LENGTH: 17
<212> TYPE: DNA
<213> ORGANISM: Artificial Sequence
<220> FEATURE:
<223> OTHER INFORMATION: Synthesized oligodeoxynucleotide, S3 5' end,
      all phosphodiester

<400> SEQUENCE: 26
cctaggggtg ggggcct                                                   17

<210> SEQ ID NO 27
<211> LENGTH: 11
<212> TYPE: DNA
<213> ORGANISM: Artificial Sequence
<220> FEATURE:
<223> OTHER INFORMATION: Synthesized oligodeoxynucleotide, S3 3' end,
      all phosphodiester

<400> SEQUENCE: 27
aggcccccac c                                                         11

```
<210> SEQ ID NO 28
<211> LENGTH: 116
<212> TYPE: DNA
<213> ORGANISM: Artificial Sequence
<220> FEATURE:
<223> OTHER INFORMATION: Synthesized oligodeoxynucleotide, dSLIM 30L1,
      all phosphodiester

<400> SEQUENCE: 28 cctagggggtt accaccttca ttggaaaacg ttcttcgggg cgttcttagg tggtaacccc    60
taggggttac caccttcatt ggaaaacgtt cttcggggcg ttcttaggtg gtaacc        116

<210> SEQ ID NO 29
<211> LENGTH: 116
<212> TYPE: DNA
<213> ORGANISM: Artificial Sequence
<220> FEATURE:
<223> OTHER INFORMATION: Synthesized oligodeoxynucleotide, dSLIM KG, all
      phosphodiester

<400> SEQUENCE: 29
ctgcagctgt agcagcttca ttccatatcg ttcttcgtgt cgttcttagc tgctacagct    60
gcagctgtag cagcttcatt ccatatcgtt cttcgtgtcg ttcttagctg ctacag       116
```